US008021876B2

(12) United States Patent
Atala et al.

(10) Patent No.: US 8,021,876 B2
(45) Date of Patent: Sep. 20, 2011

(54) METHODS OF ISOLATION, EXPANSION AND DIFFERENTIATION OF FETAL STEM CELLS FROM CHORIONIC VILLUS, AMNIOTIC FLUID, AND PLACENTA AND THERAPEUTIC USES THEREOF

(75) Inventors: Anthony Atala, Winston Salem, NC (US); Paolo De Coppi, Treviso (IT)

(73) Assignee: Children's Medical Center Corporation, Boston, MA (US)

( * ) Notice: Subject to any disclaimer, the term of this patent is extended or adjusted under 35 U.S.C. 154(b) by 0 days.

(21) Appl. No.: 10/495,419

(22) PCT Filed: Nov. 15, 2002

(86) PCT No.: PCT/US02/36966
§ 371 (c)(1),
(2), (4) Date: Jan. 21, 2005

(87) PCT Pub. No.: WO03/042405
PCT Pub. Date: May 22, 2003

(65) Prior Publication Data
US 2005/0124003 A1 Jun. 9, 2005

Related U.S. Application Data

(60) Provisional application No. 60/335,878, filed on Nov. 15, 2001, provisional application No. 60/356,295, filed on Feb. 13, 2002.

(51) Int. Cl.
*C12N 5/0789* (2010.01)
*G01N 33/50* (2006.01)
(52) U.S. Cl. ........ 435/325; 435/7.1; 435/7.21; 435/374; 435/383
(58) Field of Classification Search .......... 435/7.1, 435/7.21, 325, 374, 383
See application file for complete search history.

(56) References Cited

U.S. PATENT DOCUMENTS

| | | |
|---|---|---|
| 5,580,724 A | 12/1996 | Alter |
| 5,646,004 A | 7/1997 | Van Vlasselaer |
| 5,665,557 A | 9/1997 | Murray et al. |
| 5,672,346 A | 9/1997 | Srour et al. |
| 5,677,136 A | 10/1997 | Simmons et al. |
| 5,744,347 A | 4/1998 | Wagner et al. |
| 5,750,339 A | 5/1998 | Smith |
| 5,827,735 A | 10/1998 | Young et al. |
| 5,827,742 A | 10/1998 | Scadden |
| 5,840,502 A | 11/1998 | Van Vlasselaer et al. |
| 5,861,315 A | 1/1999 | Nakahata |
| 5,965,437 A | 10/1999 | Scadden |
| 6,200,806 B1 | 3/2001 | Thomson |
| 6,242,579 B1 | 6/2001 | Lawman et al. |
| 6,455,678 B1 | 9/2002 | Yin et al. |
| 6,461,645 B1 | 10/2002 | Boyse et al. |
| 6,555,318 B2 | 4/2003 | Keller et al. |
| 6,555,324 B1 | 4/2003 | Olweus et al. |
| 2001/0046489 A1 | 11/2001 | Habener et al. |
| 2001/0049139 A1 | 12/2001 | Lagasse et al. |
| 2001/0051372 A1 | 12/2001 | Yin et al. |
| 2002/0022268 A1* | 2/2002 | Xu et al. ............... 435/366 |
| 2002/0028510 A1 | 3/2002 | Sanberg et al. |
| 2002/0090722 A1 | 7/2002 | Dominko et al. |
| 2002/0090723 A1 | 7/2002 | Carpenter et al. |
| 2002/0123141 A1 | 9/2002 | Hariri |
| 2002/0142457 A1 | 10/2002 | Umezawa et al. |
| 2002/0160510 A1 | 10/2002 | Hariri |
| 2002/0164307 A1 | 11/2002 | Habener et al. |
| 2002/0168763 A1 | 11/2002 | Yan et al. |
| 2002/0187548 A1 | 12/2002 | Keller et al. |
| 2003/0017587 A1 | 1/2003 | Rader et al. |
| 2003/0022825 A1 | 1/2003 | Nishikawa et al. |
| 2003/0235563 A1* | 12/2003 | Strom et al. ............... 424/93.21 |

FOREIGN PATENT DOCUMENTS

| | | |
|---|---|---|
| WO | 95/26507 A1 | 10/1995 |
| WO | WO 97/41224 | 11/1997 |
| WO | 98/20731 A1 | 5/1998 |
| WO | WO 00/73421 A2 | 12/2000 |
| WO | 01/30980 A2 | 5/2001 |

OTHER PUBLICATIONS

Donovan et al. Nature 414:92-97, 2001.*
Prusa et al. Med. Sci. Monit. 8:253-257, 2002.*
Golfier et al. Br. J. Haemat. 109:173-181, 2000.*
Huss et al. Stem Cells 18:1-9; 2000.*
Kaufman et al. PNAS 98:10716-10721; 2001.*
Shamblott et al. PNAS 95:13726-13731; 1998.*
Thomson et al. Science 282:1145-1157; 1998.*
Qian, Ye et al.: "Recovery of Placental-Derived Adherent Cells with Mesenchymal Stem Cell Characteristics," *Blood*, W.B. Saunders Company, Orlando, Fl, US, vol. 98, No. 11, Part 2, Dec. 7, 2001, p. 147B, XP009026843, ISSN: 0006-4971.
De Coppi, Paolo et al.: "Human Fetal Stem Cell Isolation from Amniotic Fluid for Tissue Reconstruction" *Journal of Urology*, vol. 167, No. 4 Supplement, Apr. 2002, p. 85, XP009057017 & Annual Meeting of the American Urology Association, Inc.; Orlando, Fl, USA; May 25-30, 2002. ISSN: 0022-5347.
Sharkey, A.M. et al.: "Expression of C-Kit and Kit Ligand at the Human Maternofetal Interface," *Cytokine*, vol. 6, No. 2, 1994, pp. 195-205, XP002354029, ISSN: 1043-4666.
Saito, Shigeru et al.: "Localization of Stem Cell Factor (SCF) and C-Kit mRNA in Human Placental Cultured Cytotrophoblasts," *Biochemical and Biophysical Research Communications*, vol. 205, No. 3, 1994, pp. 1762-1769, XP002354030, ISSN: 0006-291X.
Kauma, Scott et al.: "The Expression of Stem Cell Factor and its Receptor, C-Kit in Human Endometrium and Placental Tissues During Pregnancy," *Journal of Clinical Endocrinology and Metabolism*, vol. 81, No. 3, 1996, pp. 1261-1266, XP002354028, ISSN: 0021-972X.

(Continued)

*Primary Examiner* — Anne Marie S. Wehbe
(74) *Attorney, Agent, or Firm* — Nixon Peabody LLP

(57) ABSTRACT

The present invention is directed to pluripotent fetal stem cells derived from chorionic villus, amniotic fluid, and placenta and the methods for isolating, expanding and differentiating these cells, and their therapeutic uses such as manipulating the fetal stem cells by gene transfection and other means for therapeutic applications.

14 Claims, 15 Drawing Sheets

OTHER PUBLICATIONS

Pittenger, M.F., et al.: "Multilineage Potential of Adult Human Mesenchymal Stem Cells", *Science*, American Association for the Advancement of Science, US, vol. 284, No. 5411, Apr. 2, 1999, pp. 143-147, XP000867221, ISSN: 0036-8075.

Branick et al., "Stem Cell Research: Licit or Complicit?" *Health Progress* 80(5):37-42 (1999).

Campagnoli et al., "Circulating Hematopoietic Progenitor Cells in First Trimester Fetal Blood," *Blood* 95(6):1967-1972 (2000).

Craven et al., "Review: Transfusion of Fetal Cord Blood Cells: An Improved Method of Hematopoietic Stem Cell Transplantation?" *J. Repro. Immun.* 42:59-77 (1999).

Erlich et al., "Fluorescence-Based Selection of Gene-Corrected Hematopoietic Stem and Progenitor Cells From Acid Sphingomyelinase-Deficient Mice: Implications for Niemann-Pick Disease Gene Therapy and the Development of Improved Stem Cell Gene Transfer Procedures" *Blood* 93(1):80-86 (1999).

Hall et al., "Phenotype Differentiation of TGF-β1-Responsive Pluripotent Premesenchymal Prehematopoietic Progenitor (P4 Stem) Cells from Murine Bone Marrow," *J. Hematotherapy & Stem Cell Research* 10:261-271 (2001).

Heidari et al., "Promotion of Proliferation of Murine Hematopoietic Stem Cells by Growth Factors in Murine Amniotic Fluid,"*J. Repro. Immun.* 31:51-64 (1996).

Horie et al., "The Expression of *c-kit* Protein During Oogenesis and Early Embryonic Development," *Biol. Reprod.* 45(4) 547-552 (1991).

Ikuta et al., "Evidence That Hematopoietic Stem Cells Express Mouse *c-kit* But Do Not Depend on Steel Factor for Their Generation," *PNAS* 89:1502-1506 (1992).

Ogawa et al., "Expression and Function of c-Kit in Fetal Hematopoietic Progenitor Cells: Transition From the Early c-Kit-Independent to the Late c-Kit-Dependent Wave of Hematopoiesis in the Murine Embryo," *Development* 117:1089-1098 (1993).

Ohkubo et al., "High-Efficiency Retroviral Transduction of Fetal Liver CD38-CD34++ Cells: Implications for in Utero and Ex Utero Gene Therapy," *Fetal Diagn. Ther.* 16:299-307 (2001).

Ohneda et al., "Hematopoietic Stem Cell Maintenance and Differentiation Are Supported by Embryonic Aorta-Gonad-Mesonephros Region-Derived. Endothelium," *Blood* 92(3):908-919 (1998).

Priest et al., "Origin of Cells in Human Amniotic Fluid Cultures" *Laboratory Investigation* 39(2):106-109 (1978).

Yamaguchi et al., "Umbilical Vein Endothelial Cells are an Important Source of c-kit and Stem Cell Factor Which Regulate the Proliferation of Haemopoietic Progenitor Cells" *Br. J. Haematology* 94:606-611 (1996).

Campagnoli et al., "Identification of mesenchymal stem cells in human first trimester blood, liver, and bone marrow." Blood 96:Abstract, 2000.

Shamblott, M. J. et al., "Derivation of pluripotent stem cells from cultured human primordial germ cells." PNAS 95:13726-13731, 1998.

Ikuta, K. and Weissman, I.L., Proc Natl Acad Sci USA, 89:1502-1506 (1992). "Evidence that hematopoietic stem cells express mouse c-kit but do not depend on steel factor for their generation."

* cited by examiner

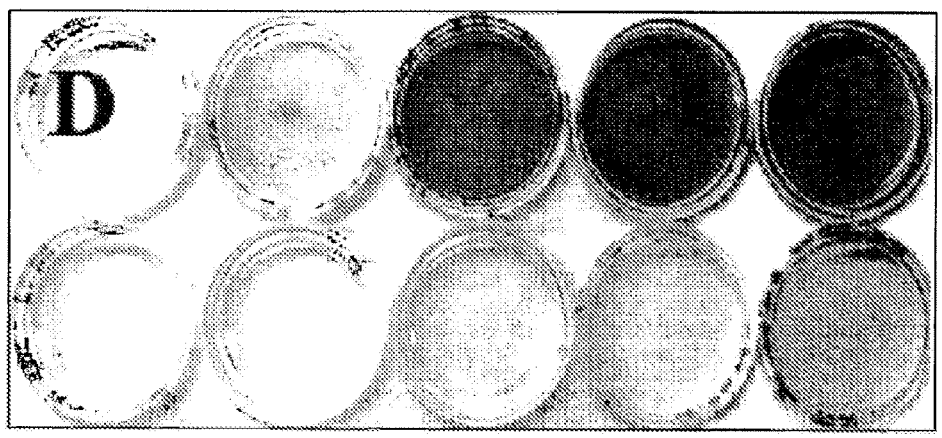
FIG. 2D
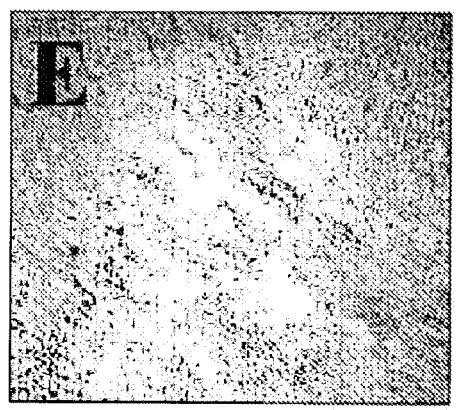 
FIG. 2E      FIG. 2F

METHODS OF ISOLATION, EXPANSION AND DIFFERENTIATION OF FETAL STEM CELLS FROM CHORIONIC VILLUS, AMNIOTIC FLUID, AND PLACENTA AND THERAPEUTIC USES THEREOF

CROSS-REFERENCE TO RELATED APPLICATIONS

This application is the U.S. National Phase Entry Under 35 U.S.C. §371 of International Application No. PCT/US02/36966, filed Nov. 15, 2002 which designated the U.S. and which claims benefit of U.S. Provisional Application Ser. No. 60/335,878 filed Nov. 15, 2001 and U.S. Provisional Application Ser. No. 60/356,295 filed Feb. 13, 2002.

FIELD OF THE INVENTION

This invention relates to the isolation, expansion and differentiation of fetal stem cells from chorionic villus, amniotic fluid, and placenta and therapeutic uses thereof.

BACKGROUND OF THE INVENTION

Stem cells are unique cell populations with the ability to undergo both renewal and differentiation. This fate choice is highly regulated by intrinsic signals and the external microenvironment. They can be identified in many adult mammalian tissues, such as bone marrow, skeletal muscle, skin and adipose tissue, where they contribute to replenishment of cells lost through normal cellular senescence or injury. Although stem cells in adult tissues may be capable of developing into more cell types than originally thought, they have a limited cellular regeneration or turnover.

Stem cells have been reported to exist during embryonic development and postnatally in bone marrow, skeletal muscle and skin. Embryonic stem (ES) cells are derived from the inner cell mass (ICM) at the blastula stage, and have the property of participating as totipotent cells when placed into host blastocysts. They are able not only to activate the expression of genes restricted to each of the three embryonic germ (EG) layers, but they are also able to express receptors for a number of different soluble growth factors with established effects on developmental pathways in vivo.

Adult stem cells, on the other hand, do not differentiate spontaneously, but can be induced to differentiate by applying appropriate growth conditions. Adult stem cells seem to be easier to maintain in culture than ES cells. Adult stem cells have the disadvantage of not being immortal, and most of them lose their pluripotency after a defined number of passages in culture. This short life-span may be a problem for clinical applications where a large amount of cells are needed.

In contrast to adult stem cells, ES cells, derived from blastocyst-stage early mammalian embryos, have the ability to give rise to cells that not only proliferate and replace themselves indefinitely, but that have the potential to form any cell type. ES cells tend to differentiate spontaneously into various types of tissues; however, specific growth induction conditions do not direct differentiation exclusively to specific cell types. Two reports describing the isolation, long-term culture, and differentiation of such cells have generated tremendous excitement in this regard and are herein incorporated by reference (Shamblott, Michael J., et al., "Derivation of Pluripotent Stem Cells from Cultured Human Primordial Germ Cells," Proc. Natl. Acad. Sci. USA, Vol. 95, pp. 13726-31, November 1998; Thomson, James A., et al., "Embryonic Stem Cell Lines Derived from Human Blastocysts," Science, Vol. 282, pp. 1145-47, Nov. 6, 1998). Although there is a great scientific interest in ES cell research, the destruction of embryos in order to harvest and experiment on ES cells still create unresolved ethical concerns.

Fetal tissue has been used in the past for autograft and allograft transplantation and tissue engineering research because of its pluripotency, proliferative ability and lack of immunogenecity. Fetal cells maintain a higher capacity to proliferate than adult cells and may preserve their pluripotency longer in culture. However, fetal cell transplants are plagued by problems that are very difficult to overcome. Fetal tissue can be currently obtained from a biopsy of the fetus itself during gestation or from cord blood at birth; however, both procedures are associated with a defined morbidity. Fetal tissue can also be obtained from aborted embryos, but this resource is limited. Beyond the ethical concerns regarding the use of cells from aborted fetuses or living fetuses, there are other issues which remain a challenge. For example, studies have shown that it generally takes about six fetuses to provide enough material to treat one patient with Parkinson's disease.

Because stem cells, particularly pluripotent stem cells appear to be an excellent resource for therapeutic applications, there is a great need for a source of stem cells that is plentiful, easy to manipulate, and avoids ethical considerations.

SUMMARY OF THE INVENTION

We have discovered that chorionic villus, amniotic fluid, and placenta provide an excellent source of pluripotent fetal stem cells for therapeutic applications. These fetal stem cells have a better potential for expansion than adult stem cells and avoid the current controversies associated with the use of human embryonic stem cells. The c-kit$^{pos}$ cells isolated from the chorionic villus, amniotic fluid and placenta samples differentiate into specific cell lineages, they do not need feeder layers to grow, and most importantly, the isolation of these cells does not require the sacrifice of human embryos for their isolation, thus avoiding the current controversies associated with the use of human embryonic stem cells.

Therefore, the present invention is directed to pluripotent fetal stem cells derived from chorionic villus, amniotic fluid, and placenta and the methods for isolating, expanding and differentiating these cells, and their therapeutic uses such as manipulating the fetal stem cells by gene transfection and other means for therapeutic applications, including but not limited to enzyme replacement and gene therapy, tissue regeneration and replacement, including, for example burn and wound dressings.

In one aspect, the present invention provides a method for obtaining pluripotent human fetal stem cells comprising obtaining a chorionic villus and/or amniotic fluid and/or placenta sample from a human subject and isolating c-kit positive cells from the sample. The invention further provides culturing or expanding the c-kit positive in a culture media before or after isolation. The chorionic villus, amniotic fluid or placenta sample may be cryopreserved before isolating or differentiating the c-kit positive cells. Alternatively, the c-kit positive cells are isolated from the sample and then cryopreserved. The cells may be cryopreserved before or after differentiation.

In yet another aspect, the present invention provides a method for differentiating the isolated pluripotent human fetal stem cells derived from chorionic villus and/or amniotic fluid and/or placenta to cells of different lineages, including, but not limited to, osteogenic, adipogenic, myogenic, neurogenic, hematopoitic and endothelial lineages. Differentiation can be evidenced by, for example, changes in cellular morphology and gene expression.

In a further aspect, the present invention provides a method for differentiating c-kit positive fetal stem cells contained within a chorionic villus sample, amniotic fluid sample or a placenta sample to cells of different lineages, including, but not limited to, osteogenic, adipogenic, myogenic, neurogenic, hematopoietic, hepatic and endothelial lineages. The method comprises exposing the sample to one or more differentiation-inducing agents either in vivo or in vitro. Cells may be isolated from the sample before differentiation.

In yet another aspect, the present invention provides a method for assessing viability, proliferation potential, and longevity of the pluripotent human fetal stem cells derived from chorionic villus, amniotic fluid and placenta.

In another aspect the invention provides a method of treating disease in a human comprising administering to a human in need thereof a substantially enriched population of cells comprising pluripotent c-kit positive human fetal stem cells which have been differentiated to a lineage selected from osteogenic, hematopoietic, adipogenic, myogenic, hepatic, neurogenic and endothelial cell lineage. For example, Parkinson's disease can be treated with the isolated pluripotent c-kit positive stem cells of the present invention either directly, or after differentiating such cells into a neuronal cell lineage capable of producing dopamine.

The invention further provides a method of transplanting into a human in need thereof a substantially enriched population of cells comprising pluripotent c-kit positive human fetal stem cells which have been differentiated to a lineage selected from osteogenic, hematopoietic, adipogenic, myogenic, hepatic, neurogenic and endothelial phenotype.

In another aspect, the invention provides a composition suitable for bonemarrow transplantation comprising a substantially enriched population of cells comprising pluripotent c-kit positive human fetal stem cells which have been differentiated to a lineage selected from osteogenic, hematopoietic, adipogenic, myogenic, hepatic, neurogenic and endothelial phenotype.

Further, the invention provides a method of obtaining a population of cells enriched for pluripotent fetal stem cells, comprising isolating a tissue specimen from the chorionic villus of a human placenta.

The invention also provides a method of obtaining a population of cells enriched for pluripotent fetal stem cells, comprising isolating a tissue specimen containing said cells from human placenta, chorionic villus or amniotic fluid.

In yet another aspect the invention provides a method of obtaining a population of cells enriched for pluripotent fetal stem cells, comprising selecting c-kit positive cells from placenta.

The invention further provides a method of obtaining a population of cells enriched for pluripotent fetal stem cells, comprising the steps of cryopreseverving a tissue specimen from the chorionic villus, amniotic fluid or placenta, and thawing the cryopreserved specimen at a later date and selecting c-kit positive cells.

In another aspect, the invention provides a method of producing a population of cells enriched for pluripotent fetal stem cells comprising isolating c-kit positive cells from the chorionic villus, placenta or amniotic fluid, and proliferating the cells in culture medium.

In another aspect, the invention provides a method of producing differentiated tissue comprising providing a tissue specimen from chorionic villus, amniotic fluid or placenta, culturing the tissue under conditions that cause c-kit positive cells to proliferate; and upon induction cause the c-kit positive cells to differentiate.

The invention also provides a method of the invention provides a method of obtaining a population of cells enriched for pluripotent fetal stem cells, comprising isolating a tissue specimen from the chorionic villus of a human placenta, placenta, or amniotic fluid further comprising using negative selection to enrich c-kit positive cells from the chorionic villus.

In yeat another aspect, the invention provides a method of obtaining a population of cells enriched for pluripotent fetal stem cells, comprising isolating a tissue specimen containing said cells from human placenta, chorionic villus or amniotic fluid wherein the cells are subsequently cryopreserved.

Finally, the present invention provides therapeutic applications for the fetal stem cells derived from a chorionic villus and/or an amniotic fluid and/or a placenta sample including, but not limited to (a) autologous/heterologous enzyme replacement therapy; (b) autologous/heterologous transgene carriers in gene therapy; (c) autologous/heterologous tissue regeneration/replacement therapy; (d) reconstructive treatment by surgical implantation; (e) reconstructive treatment of tissues with products of these cells; and (f) tissue engineering.

BRIEF DESCRIPTION OF THE DRAWINGS

FIGS. 2A-2L demonstrate osteogenic induction of the c-kit$^{pos}$ cells isolated from chorionic villi and amniotic fluid. The shape of chorionic villi and amniotic c-kit$^{pos}$ cells treated with osteogenic-inducing medium after 4 days of induction changed to an osteoblast-like appearance [2A], whereas cells in the control medium did not lose their spindle-shaped phenotype [2B]. Alkaline phosphatase activity was quantified in c-kit$^{pos}$ cells that were incubated with osteogenic-inducing and control medium for 32 days [2C]. Numbers represent alkaline phosphatase production in nMol p-Nitrophenyl/min/$10^6$ cells, showing a peak of production at day 16 (solid line); whereas c-kit$^{pos}$ cells grown in control medium (shaded line) or c-kit$^{neg}$ cells grown in osteogenic conditions (dotted line) did not show any alkaline phosphatase production. C-kit$^{pos}$ cells treated with osteogenic-inducing medium and with control medium stained for alkaline phosphatase after 4, 8, 16, 24 and 32 days [2D]. Strong alkaline phosphatase staining was noted in the osteogenic-induced cells starting at day 16, and remained high thereafter. C-kit$^{pos}$ cells grown in control medium did not show any alkaline phosphatase staining.

Figure 1A:
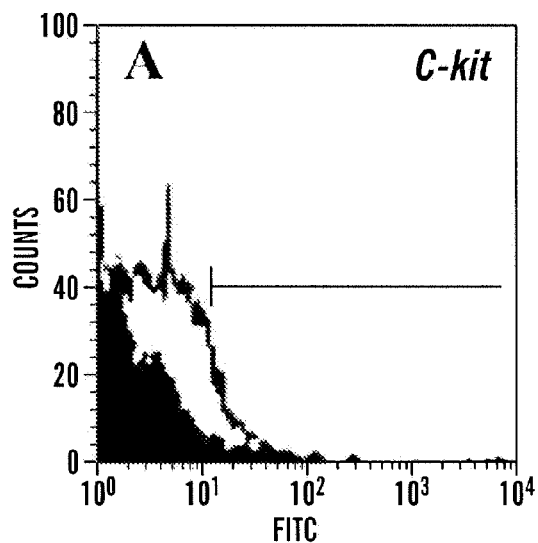
FIGS. 1A-1G show results from chorionic villi and amniotic cell characterization experiments. Between 0.8 and 3% of the amniotic and chorionic villi cells were c-kit$^{pos}$ [1A]. The c-kit$^{pos}$ cells did not stain with mouse stage specific embryonic antigen 1 [1B], but stained positively for human stage specific embryonic antigens 3 and 4 [1C and 1D]. Analyses of late passage c-kit$^{pos}$ cells (PD 200) showed a normal karyotype [1E]. Telomerase activity was evaluated using the Telomerase Repeat Amplification Protocol (TRAP) assay [1F]. The chorionic villi and amniotic c-kit$^{pos}$ cells were telomerase positive (lane 1). Upon differentiation into specific lineages, telomerase activity diminished to undetectable levels (Lane 2). Lane 3 shows the positive control. Lane 4 represents negative control cell lysate, showing no telomerase activity. The telomeric length was evaluated by terminal restriction fragment (TRF) measurement [1G]. C-kit$^{pos}$ cells had similar telomere lengths, both at early and late passages (250 PD) (lane 3 and 4, respectively) as compared with a high molecular weight marker, approximately 10.2 kbp (lane 2). Lane 1 represents a low molecular weight marker.

When confluent, the cells formed typical lamellar structures similar to those found in bone [2F]. C-kit$^{pos}$ cells in control medium did not form any lamellar structures [2E]. Mineralization of cells was quantified using a chemical assay for calcium [2G]. Numbers represent calcium deposition in mg/dl. Osteogenic-induced ckit$^{pos}$ cells showed a significant increase of calcium deposition starting at day 16 (solid line). No calcium deposition was detected in ckit$^{pos}$ cells grown in control medium (shaded line) or ckit$^{pos}$ cells grown in osteogenic conditions (dotted line). Furthermore cells treated with control medium or with osteogenic-inducing medium were analyzed using von Kossa staining after 32 days in culture (40×). The osteogenic-induced cells showed significant mineralization starting at day 16 [2H]. No mineralization occurred at any time point in cells grown in control medium [2I]. RNA was isolated from amniotic c-kit$^{pos}$ cells grown in control medium (lanes 1, 2, 3 and 4) and osteogenic-inducing medium (lanes 5, 6, 7 and 8). RT-PCR was performed using primers for alkaline phosphatase, cbfa1, osteocalcin and β2-microglobulin at days 8, 16, 24 and 32 [2G]. RT-PCR showed upregulation of cbfa1 and osteocalcin at day 8 and it confirmed the upregulation of alkaline phosphatase in the osteogenic-induced cells [2J]. C-kit$^{pos}$ cells were seeded on hydroxyapatite-collagen scaffolds, induced into an osteogenic lineage, implanted subcutaneously in athymic mice, and harvested after 4 and 8 weeks. Bone-like tissue was evident, surrounded by an extracellular matrix. Toluidine blue staining confirmed the osteogenic phenotype. Large calcified areas within the implanted tissue stained positively with von Kossa, indicating bone formation [2K]. Non seeded scaffold were implanted and used as control [2L].

FIGS. 3A-3F demonstrate adipogenic induction of the c-kit$^{pos}$ cells isolated from chorionic villi and amniotic fluid. Clusters of adipocytes appeared at 8 days [3A], and the percentage of cells increased with time until Oil-O-Red was uniformly staining the adipogenesis-induced cells at day 16 [3B]. C-kit$^{pos}$ cells cultured in control medium did not show any lipid deposits at day 16 [3C]. RNA was isolated from c-kit$^{pos}$ cells grown in control (lanes 1 and 2) and adipogenic-inducing (lanes 3 and 4) medium [3D]. RT-PCR was performed using primers for PPARγ2, lipoprotein lipase and β2-microglobulin at days 8 and 16, as indicated. Upregulation of PPARγ2 and lipoprotein lipase in cells grown in adipogenic-inducing medium was noted at days 8 and 16 (lanes 3 and 4). C-kit$^{pos}$ cells were seeded on polyglycolic acid polymer scaffolds. Cells were induced into an adipogenic lineage. The scaffolds were implanted subcutaneously in athymic mice, harvested after 4 and 8 weeks and analyzed. The retrieved scaffolds showed the formation of fatty tissues grossly [3E]. The presence of adipose tissue was confirmed with Oil-O-Red staining (200× magnification) [3F].

FIGS. 4A-4I demonstrate myogenic induction of the c-kit$^{pos}$ cells isolated from chorionic villi and amniotic fluid. Under myogenic conditions the c-kit$^{pos}$ cells fused into multi-nucleated cells at day 4 [4A] and formed myotube-like structures after 8 days [4B]. Multinucleated cells stained green for sarcomeric tropomyosin [4C] and desmin [4D] expression 16 days after myogenic induction. Cell nuclei were stained blue using DAPI. Untreated cells did not stain for sarcomeric tropomyosin [4E] or desmin [4F]. RNA was isolated from c-kit$^{pos}$ cells grown in control (lanes 1 and 2) and myogenic-inducing (lanes 3 and 4) medium [4G]. RT-PCR was performed using primers for MyoD, MRF4 (herculin, Myf6), and desmin at days 8 and 16. Myogenic-induced cells showed a strong upregulation of desmin expression at day 16 (lane 4). MyoD and MRF4 were induced with myogenic treatment at day 8 (lane 1). Specific PCR amplified DNA fragments of MyoD, MRF4 and Desmin could not be detected in the control cells at days 8 and 16 (lanes 1 and 2). C-kit$^{pos}$ cells were labeled with the fluorescence marker PKH26 and were induced into a myogenic lineage. The myogenic cells were injected into the hindlimb musculature of athymic mice and were retrieved after 4 weeks. The injected myogenic cells showed the formation of muscle tissue (m) which expressed desmin [4H] and maintained its fluorescence [4I]. The native muscle (n) did not express any fluorescence.

FIGS. 5A-5F demonstrate endothelial induction of the c-kit$^{pos}$ cells isolated from chorionic villi and amniotic fluid. Ckit$^{pos}$ cells were cultured as monolayers in PBS-gelatin coated dishes with EBM-2 and bFGF and showed a typical endothelial appearance in vitro [5A]. The fully differentiated endothelial cells stained for the endothelial specific markers FVIII [5B], KDR [5C] and P1H12 [5D]. Once cultured in matrigel the cells were able to form capillary structures over time [5E]. In order to confirm the phenotypic changes we performed RT-PCR 5[F]. CD31 and VCAM showed a marked increased in the ckit$^{pos}$ cells induced in endothelial medium (lane 2). Ckit$^{pos}$ cells cultured in control medium (lane 1) did not show any gene amplification.

FIGS. 6A-6E demonstrate neurogenic induction of the c-kit$^{pos}$ cells isolated from chorionic villi and amniotic fluid. Ckit$^{pos}$ cells cultured under neurogenic inducing conditions changed their morphology within the first 24 hours. The cell cytoplasm retracted towards the nucleus, forming contracted multipolar structures, with primary and secondary branches, and cone-like terminal expansions [6A]. The differentiated cells stained for specific neurogenic markers β III Tubulin [6B], Nestin [6C], and glial fibrillary acidic protein (GFAP) [6D]. Only the C-kit$^{pos}$ cells cultured under neurogenic conditions showed the secretion of glutamic acid in the collected medium. Furthermore the secretion of glutamic acid could be induced (KCl; 20 min in 50 mM KCl buffer) [6E].

DETAILED DESCRIPTION OF THE INVENTION

The present invention is based upon a discovery that chorionic villus, amniotic fluid, and placenta cells can be used to obtain a population of stem cells which are comparable to embryonic stem cells in their pluripotent differentiation capacity and therefore are a viable source of stem cells that can be used therapeutically.

Chorionic villus sampling and amniocentesis are well established techniques for the collection of tissue from the human embryo (10 to 12 weeks) and for the collection of fluid from the human fetus (12 weeks to term), respectively. Chorionic villus sampling is performed on pregnant mammal, preferably human, and has been in use since the 1980s. This procedure involves taking a sample of the chorion frondosum—that part of the chorionic membrane containing the villi. The chorionic membrane is the outer sac which surrounds the developing fetus. Chorionic villi are microscopic, finger-like projections that emerge from the chorionic membrane and eventually form the placenta. The cells that make up the chorionic villi are of fetal origin.

In humans, chorionic villus sampling is best performed between 10 and 12 weeks of pregnancy. The procedure is performed either through the vagina and the cervix (transcervically) or through the abdomen (transabdominally) depending upon the preferences of the patient or the doctor. In some cases, the location of the placenta dictates which method the doctor uses. For the transcervical procedure, the woman lies on an examining table on her back with her feet in stirrups. The woman's vaginal area is thoroughly cleansed with an antiseptic, a sterile speculum is inserted into her vagina and opened, and the cervix is cleansed with an antiseptic. Using ultrasound (a device which uses sound waves to visualize internal organs) as a guide, the doctor inserts a thin, plastic tube called a catheter through the cervix and into the uterus. The passage of the catheter through the cervix may cause cramping. The doctor carefully watches the image produced by the ultrasound and advances the catheter to the chorionic villi. By applying suction from the syringe attached to the other end of the catheter, a small sample of the chorionic villi are obtained. A cramping or pinching feeling may be felt as the sample is being taken. The catheter is then easily withdrawn.

For the transabdominal method, the woman lies on her back on an examining table. Ultrasound enables the doctor to locate the placenta. The specific area on the woman's abdomen is cleansed thoroughly with an antiseptic and a local anesthetic may be injected to numb the area. With ultrasound guidance, a long needle is inserted through the woman's abdominal wall, through the uterine wall and to the chorionic villi. The sample is obtained by applying suction from the syringe. The chorionic villus sample is immediately placed a into nutrient medium.

Amniotic fluid is obtained using amniocentesis. The word amniocentesis literally means "puncture of the amnion," the thin-walled sac of fluid in which a developing fetus is suspended during pregnancy. During the sampling procedure, the obstetrician inserts a very fine needle through the woman's abdomen into the uterus and amniotic sac and withdraws approximately one ounce of amniotic fluid.

The physician uses ultrasound images to guide needle placement and collect the sample, thereby minimizing the risk of fetal injury and the need for repeated needle insertions. Once the sample is collected, the woman can return home after a brief observation period. She may be instructed to rest for the first 24 hours and to avoid heavy lifting for two days. Consequently, the fetal cells contained in the fluid are isolated and grown as explained below.

These techniques may be used to obtain chorionic villus and amniotic fluid samples in accordance with the present invention. Cultured cells from the chorionic villi or amniotic fluid of pregnancies have been used widely for the prenatal diagnosis of genetic disorders. The morphologic heterogeneity of these cells is well known. Numerous cell types from all 3 germ layers are found in the placenta and the amniotic fluid at different levels of differentiation (6). Large quantities of chorionic villi and amniotic fluid are available during pregnancy and at the time of birth, and cells can be easily obtained from these sources. The same is true for placenta, which is obtainable after birth.

A sample of placenta may be obtained using a punch-biopsy, a scalpel or homogenizing the placenta or a portion thereof using, for example, a blender. The homogenate may then be used as a source of cells.

Stem cell differentiation requires cell-cell contact and cell-extracellular matrix interactions. While not wishing to be bound by a particular theory, it is believed that chorionic villus, amniotic fluid and placenta make a good source of undifferentiated cells because the cells liberated in the chorionic villus and amniotic fluid from the fetus during development may not receive any signal of differentiation, and may be able to maintain their "pluripotential" state. We have discovered that the preferred cells are c-kit positive. Thus, the c-kit marker can be used to isolate these cells. As used herein the terms "pluripotent" or "pluripotential" cell refers to a cell that has complete differentiation versatility, i.e., the capacity to differentiate into at least osteogenic phenotype, hematopoietic phenotype, adipogenic phenotype, myogenic phenotype, hepatic phenotype and endothelial phenotype in appropriate inducing conditions, preferably the pluripotent cell has the capacity to differentiate to any of the mammalian body's about 260 different cell types.

The c-kit gene encodes a tyrosine kinase growth factor receptor for Stem Cell Factor (SCF), also called mast cell growth factor, that is essential for hematopoiesis, melanogenesis and fertility. The larger 45 kDa form is processed to generate a 31 kDa soluble factor while the smaller 32 kDa form gives rise to a 23 kDa factor. Expression of the two alternatively spliced forms is somewhat tissue-specific; the 31 kDa form of SCF is expressed in fibro-blasts and thymus tissue while the 23 kDa factor is found in spleen, testis, placenta and cerebellum. The c-kit receptor protein, also known as c-Kit receptor, Steel factor receptor, stem cell factor receptor and CD117 in standardized terminology of leukocyte antigens, is constitutively expressed in hematopoietic stem cells, mast cells, germ cells, melanocytes, certain basal epithelial cells, luminal epithelium of breast, and the interstitial cells of Cajal of the gastrointestinal tract. The c-kit receptor plays a fundamental role during the establishment, maintenance and function of germ cells. In the embryonal gonad the c-kit receptor and its ligand SCF are required for the survival and proliferation of primordial germ cells. In the postnatal animal, c-kit/SCF are required for production of the mature gametes in response to gonadotropic hormones, i.e. for the survival and/or proliferation of the only proliferating germ cells of the testis, the spermatogonia, and for the growth and maturation of the oocytes. Experiments have shown that c-kit is a potent growth factor for primitive hematopoietic cell proliferation in vitro. In mice, loss of either SCF or c-kit due to mutations in their loci results in macrocytic anemia, leading to death in utero or within the first postnatal days.

Antibodies reactive with the c-kit or portions thereof can be used to isolate c-kit positive cells. In a preferred embodiment, the antibodies specifically bind with the c-kit or a portion thereof. The antibodies can be polyclonal or monoclonal, and the term antibody is intended to encompass polyclonal and monoclonal antibodies, and functional fragments thereof. The terms polyclonal and monoclonal refer to the degree of homogeneity of an antibody preparation, and are not intended to be limited to particular methods of production.

Therefore, examples of antibodies useful according to the present invention include antibodies recognizing the c-kit. Such antibodies are herein referred to as "c-kit antibodies." Examples of commercially available useful c-kit antibodies include, but are not limited to antibodies in table 1, that can be purchased from Santa Cruz Biotechnology, Inc.

| Antibody | Cat.# | Isotype | Epitope | Applications | Species |
| --- | --- | --- | --- | --- | --- |
| SCF (N-19) | sc-1302 | goat IgG | N-terminus (h) | WB, IP, IHC, ELISA | human |
| c-Kit (C-19) | sc-168 | rabbit IgG | C-terminus (h) | WB, IP, IHC, PAR | mouse, rat, human |

-continued

| Antibody | Cat.# | Isotype | Epitope | Applications | Species |
|---|---|---|---|---|---|
| c-Kit (M-14) | sc-1494 | goat IgG | C-terminus (m) | WB, IP, IHC | mouse, rat, human |
| c-Kit (Ab 81) | sc-13508 | mouse IgG$_1$ | FL (h) | WB, IP, IHC FCM | human |
| c-Kit (C-14) | sc-1493 | goat IgG | C-terminus (h) | WB, IP, IHC | human> mouse |
| c-Kit (104D2) | sc-19983 | mouse IgG$_1$ | n/a | IHC, FCM | human |
| c-Kit (H-300) | sc-5535 | rabbit IgG | 23-322 (h) | WB, IP, IHC | mouse rat, human |
| c-Kit (E-1) | sc-17806 | mouse IgG$_1$ | 23-322 (h) | WB, IHC | human |

The preferred antibody is c-Kit (E-1), which is a mouse monoclonal igG recognizing an epitope corresponding to amni acids 23-322 mapping near the c-kit N-temminys and recognizes both c-Kit of human origin by both Western blotting and immunihistochemistry.

Additional examples of commercially available antibodies include, but are not limited to YB5.B8 monoclonal antibody, specific for human CD117 (eBioscience, San Diego, Calif.); an antibody produced against a human leucaemic cell line UT7 transfected with CD117 cDNA (Chemicon International, Temecula, Calif.); a polyclonal antibody produced against the C-terminal end of CD117 (Assay Designs Inc., Ann Arbor, Mich., catalog No. 90572); clone 28 c-kit monoclonal antibody (catalog no. 612318, from BD Transduction Laboratories, Franklin Lakes, N.J.); a c-kit tyrosine kinase receptor antibody ab1462, which is a rabbit polyclonal anti-human c-kit tyrosine kinase receptor antibody was generated using a synthetic KLH-conjugated peptide corresponding to the carboxy-terminus of the CD117; and a monoclonal 13CD anti c-kit antibody from Zymed Laboratories Inc. (South San Francisco, Calif.).

Further, antibodies recognizing c-kit or fragments thereof may be obtained or prepared as discussed in U.S. Pat. No. 5,454,533, incorporated herein by reference. The c-kit antigen can be contacted with an antibody, such as various c-kit monoclonal antibodies, which have specificity for the c-kit antigen. A c-kit antibody is characterized by binding to the c-kit protein or fragments thereof under Western blot conditions from reducing SDS-PAGE gels. For example, the CD117 antigen of c-kit has a molecular weight, based on commercially available standards, in the range of about 145 kDa.

The terms "specific binding" or "specifically binding", as used herein, refers to the interaction between a c-kit or a fragment thereof expressed by a cell present in a chorionic villus, amniotic fluid or placenta sample, and an antibody. The interaction is dependent upon the presence of a particular structure, i.e., the antigenic determinant or epitope of c-kit, of the c-kit recognized by the binding molecule, i.e. the c-kit antibody. For example, if an antibody is specific for epitope "A" of c-kit, the presence of a protein containing epitope A (or free, unlabeled A) in a reaction containing labeled "A" and the antibody will reduce the amount of labeled A bound to the antibody.

Additionally, antibodies to c-kit antigen or fragments thereof can be obtained by immunizing a xenogeneic immunocompetent mammalian host (including murine, rodentia, lagomorpha, ovine, porcine, bovine, etc.) with human c-kit or fragments thereof expressing cells. The choice of a particular host is primarily one of convenience. A suitable progenitor cell population for immunization can be obtained, for example by isolating c-kit positive cells from tissues or cell cultures. Immunizations are performed in accordance with conventional techniques, where the cells may be injected subcutaneously, intramuscularly, intraperitoneally, intravascularly, etc. Normally, from about $10^6$ to $10^8$ cells will be used, which may be divided up into one or more injections, usually not more than about 8 injections, over a period of from about one to three weeks. The injections may be with or without adjuvant, e.g. complete or incomplete Freund's adjuvant, specol, alum, etc.

After completion of the immunization schedule, the antiserum may be harvested in accordance with conventional ways to provide polygonal antisera specific for the surface membrane proteins of progenitor cells, including the c-kit antigen or fragments thereof. Lymphocytes are harvested from the appropriate lymphoid tissue, e.g. spleen, draining lymph node, etc., and fused with an appropriate fusion partner, usually a myeloma line, producing a hybridoma secreting a specific monoclonal antibody. Screening clones of hybridomas for the antigenic specificity of interest is performed in accordance with conventional methods.

Antibodies against c-kit or fragments thereof can be produced as a single chain, instead of the normal multimeric structure. Single chain antibodies are described in Jost et al., 269 J. Biol. Chem. 26267-73 (1994), incorporated herein by reference, and others. DNA sequences encoding the variable region of the heavy chain and the variable region of the light chain are ligated to a spacer encoding at least about 4 amino acids of small neutral amino acids, including glycine or serine. The protein encoded by this fusion allows assembly of a functional variable region that retains the specificity and affinity of the original antibody.

Antibodies against c-kit or fragments thereof can be produced by use of Ig cDNA for construction of chimeric immunoglobulin genes (Liu et al., 84 Proc. Natl. Acad. Sci. 3439 (1987) and 139 J. Immunol. 3521 (1987), incorporated herein by reference. mRNA is isolated from a hybridoma or other cell producing the antibody and used to produce cDNA. The cDNA of interest may be amplified by the polymerase chain reaction using specific primers (U.S. Pat. Nos. 4,683,195 and 4,683,202). Alternatively, a library is made and screened to isolate the sequence of interest. The DNA sequence encoding the variable region of the antibody is then fused to human constant region sequences. The sequences of human constant regions genes may be found in Kabat et al., "Sequences of Proteins of Immunological Interest" N.I.H. publication No. 91-3242 (1991). Human C region genes are readily available from known clones. The chimeric, humanized antibody is then expressed by conventional methods.

Antibodies against c-kit or fragments thereof can also be produced as antibody fragments, such as Fv, F(ab')$_2$ and Fab. Antibody fragments may be prepared by cleavage of the intact protein, e.g. by protease or chemical cleavage. Alternatively, a truncated gene is designed. For example, a chimeric gene encoding a portion of the F(ab')$_2$ fragment would include DNA sequences encoding the CH1 domain and hinge region of the H chain, followed by a translational stop codon to yield the truncated molecule.

The c-kit positive cell selection can be by any suitable means known in the art, including flow cytometry, such as by fluorescence activated cell sorting using a fluorochrome conjugated c-kit antibody. The selection can also be by high gradient magnetic selection using c-kit antibody is conjugated to magnetic particles. Any other suitable method including attachment to and disattachment from solid phase, is also contemplated within the scope of the invention.

One of skill in the art can derive the population of cells by immunoselection using an c-kit antibody. The population of cells should contain at least 30% c-kit positive (c-kit$^+$ or c-kit$^{pos}$) pluripotent fetal stem cells, preferably at least 50-70% c-kit$^+$ fetal stem cells, and more preferably greater than 90% c-kit$^+$ fetal stem cells. Most preferable would be a substantially pure population of c-kit$^+$ fetal stem cells, comprising at least 95% c-kit$^+$ fetal stem cells.

The number of c-kit positive cells in a cell population can be determined in any well known method known to one skilled in the art. For example, FACS analysis can be used as shown in FIG. 1A. Alternatively, magnetic cell sorting technology (MACS) can be used to separate cells (see, e.g. Miltenyi Biotech, Inc., Auburn, Calif.). In MACS, the c-kit positive cells can be separated from the mixture of chorionic villus cells, amniotic fluid, and placenta cells to very high purity. The c-kit positive cells are specifically labeled with superparamagnetic MACS MicroBeads which can be designed to bind to either the c-kit antigen directly or to the antibody recognizing c-kit. After magnetic labeling, the cells are passed through a separation column which is placed in a strong permanent magnet. The column matrix serves to create a high-gradient magnetic field. The magnetically labeled cells are retained in the column while non-labeled cells pass through. After removal of the column from the magnetic field, the magnetically retained cells are eluted. Both labeled and non-labeled fractions can be completely recovered.

The in vitro cell cultures described herein containing an enriched population of c-kit positive pluripotent fetal stem cells are generally characterized in that the cultures stain positive for c-kit and SSAE3 and SSAE4, produce progeny cells that can differentiate into at least two, preferably three, most preferably at least all of the following cell lineages: osteogenic, adipogenic, neurogenic, myogenic, hematopoietic, hepatic and endothelial cell lineages in the presence of differentiation-inducing conditions of which examples are described in the Example below. Further examples of differentiation-inducing agent and combinations thereof for differentiating desired cell lineages can be found at Stem Cells: Scientific Progress and Future Research Directions. (Appendix D. Department of Health and Human Services. June 2001. www.nih.gov/news/stemcell/scireport.htm)

Immunostaining. Biological samples including the cells isolated from chrorionic villus samples, amniotic fluid samples or placenta are assayed for the presence of c-kit$^+$ fetal stem cells by any convenient immunoassay method for the presence of cells expressing the c-kit, bound by the c-kit antibodies. Assays may be performed on cell lysates, intact cells, frozen sections, etc.

Cell Sorting. The use of cell surface antigens to fetal stem cells, such as c-kit provides a means for the positive immunoselection of fetal stem cell populations, as well as for the phenotypic analysis of progenitor cell populations using, for example, flow cytometry. Cells selected for expression of c-kit antigen may be further purified by selection for other stem cell and progenitor cell markers, including, but not limited to SSAE3 and SSAE4 human embryonic stem stage specific markers.

Alternatively, for the preparation of substantially pure pluripotent fetal stem cells, a subset of stem cells can be separated from other cells on the basis of c-kit antibody binding and the c-kit positive fetal stem cells may be further separated by binding to other surface markers known in the art.

Procedures for separation may include magnetic separation, using antibody-coated magnetic beads, affinity chromatography and "panning" with antibody attached to a solid matrix, e.g. plate, or other convenient technique. Techniques providing accurate separation include fluorescence activated cell sorters, which can have varying degrees of sophistication, such as multiple color channels, low angle and obtuse light scattering detecting channels, impedance channels, etc. Dead cells may be eliminated by selection with dyes associated with dead cells (propidium iodide (PI), LDS). Any technique may be employed which is not unduly detrimental to the viability of the selected cells.

Conveniently, the antibodies are conjugated with labels to allow for ease of separation of the particular cell type, e.g. magnetic beads; biotin, which binds with high affinity to avidin or streptavidin; fluorochromes, which can be used with a fluorescence activated cell sorter; haptens; and the like. Multi-color analyses may be employed with the FACS or in a combination of immunomagnetic separation and flow cytometry. Multi-color analysis is of interest for the separation of cells based on multiple surface antigens, e.g. c-kit$^+$, and antibodies recognizing SSAE3 and SSAE4 cell markers. Fluorochromes which find use in a multi-color analysis include phycobiliproteins, e.g. phycoeryirin and allophycocyanins; fluorescein and Texas red. A negative designation indicates that the level of staining is at or below the brightness of an isotype matched negative control. A dim designation indicates that the level of staining may be near the level of a negative stain, but may also be brighter than an isotype matched control.

In one embodiment, the c-kit antibody is directly or indirectly conjugated to a magnetic reagent, such as a superparamagnetic microparticle (microparticle). Direct conjugation to a magnetic particle is achieved by use of various chemical linking groups, as known in the art. Antibody can be coupled to the microparticles through side chain amino or sufhydryl groups and heterofunctional cross-linking reagents. A large number of heterofunctional compounds are available for linking to entities. A preferred linking group is 3-(2-pyridyidithio)propionic acid N-hydroxysuccinimide ester (SPDP) or 4-(N-maleimidomethyl)-cyclohexane-1-carboxylic acid N-hydroxysuccinimide ester (SMCC) with a reactive sulfhydryl group on the antibody and a reactive amino group on the magnetic particle.

Alternatively, c-kit antibody is indirectly coupled to the magnetic particles. The antibody is directly conjugated to a hapten, and hapten-specific, second stage antibodies are conjugated to the particles. Suitable haptens include digoxin, digoxigenin, FITC, dinitrophenyl, nitrophenyl, avidin, biotin, etc. Methods for conjugation of the hapten to a protein, i.e. are known in the art, and kits for such conjugations are commercially available.

To practice the method, the c-kit antibody (Ab) is added to a cell sample. The amount of c-kit Ab necessary to bind a particular cell subset is empirically determined by performing a test separation and analysis. The cells and c-kit antibody are incubated for a period of time sufficient for complexes to form, usually at least about 5 min, more usually at least about 10 min, and usually not more than one hr, more usually not more than about 30 min.

The cells may additionally be incubated with antibodies or binding molecules specific for cell surface markers known to be present or absent on the fetal stem cells. For example, cells expressing SSAE1 marker can be negatively selected for.

The labeled cells are separated in accordance with the specific antibody preparation. Fluorochrome labeled antibodies are useful for FACS separation, magnetic particles for immunomagnetic selection, particularly high gradient magnetic selection (HGMS), etc. Exemplary magnetic separation devices are described in WO 90/07380, PCT/US96/00953, and EP 438,520.

The purified cell population may be collected in any appropriate medium. Various media are commercially available and may be used, including Dulbecco's Modified Eagle Medium (DMEM), Hank's Basic Salt Solution (HBSS), Dulbecco's phosphate buffered saline (dPBS), RPMI, Iscove's modified Dulbecco's medium (IMDM), phosphate buffered saline (PBS) with 5 mM EDTA, etc., frequently supplemented with fetal calf serum (FCS), bovine serum albumin (BSA), human serum albumin (HSA), etc. Preferred culture media include DMEM, F-12, M1 99, RPMI.

Populations highly enriched for pluripotent fetal stem cells are achieved in this manner. The desired cells will be 30% or more of the cell composition, preferably 50% or more of the cell population, more preferably 90% or more of the cell population, and most preferably 95% or more (substantially pure) of the cell population.

The use of substantially purified or enriched c-kit positive pluripotent fetal stem cells of the present invention are useful in a variety of ways. The c-kit positive cells can be used to reconstitute a host whose cells have been lost through disease or injury. Genetic diseases associated with cells may be treated by genetic modification of autologous or allogeneic stem cells to correct a genetic defect or treat to protect against disease.

Alternatively, normal allogeneic fetal stem cells may be transplanted. Diseases other than those associated with cells may also be treated, where the disease is related to the lack of a particular secreted product such as hormone, enzyme, growth factor, or the like. CNS disorders encompass numerous afflictions such as neurodegenerative diseases (e.g. Alzheimer's and Parkinson's), acute brain injury (e.g. stroke, head injury, cerebral palsy) and a large number of CNS dysfunctions (e.g. depression, epilepsy, and schizophrenia). In recent years neurodegenerative disease has become an important concern due to the expanding elderly population which is at greatest risk for these disorders. These diseases, which include Alzheimer's Disease, Multiple Sclerosis (MS), Huntington's Disease, Amyotrophic Lateral Sclerosis, and Parkinson's Disease, have been linked to the degeneration of neural cells in particular locations of the CNS, leading to the inability of these cells or the brain region to carry out their intended function. By providing for maturation, proliferation and differentiation into one or more selected lineages through specific different growth factors the progenitor cells may be used as a source of committed cells. The pluripotent fetal stem cells according to the present invention can also be used to produce a variety of blood cell types, including myeloid and lymphoid cells, as well as early hematopoietic cells (see, Bjornson et al., 283 Science 534 (1999), incorporated herein by reference).

A variety of cell differentiation inducing agents can be use to differentiate the pluripotent fetal stem cells of the present invention into different phenotypes. To determine the differentiation status of the stem cells, the phenotypic characteristic of the cells are observed using conventional methods such as light microscopy to detect cell morphology (see, e.g., FIGS. 2-6), RT-PCT to detect cell lineage specific transcription, and immunocytochemistry to detect cell surface markers specifically expressed in a particulate cell lineage. For example, genes expressed during the osteogenic differentiation serve as markers of the stem cells differentiating into osteogenic lineage (Long, Blood Cells Mol Dis 2001 May-June; 27(3):677-90).

The c-kit positive fetal stem cells may also be used in the isolation and evaluation of factors associated with the differentiation and maturation of cells. Thus, the cells may be used in assays to determine the activity of media, such as conditioned media, evaluate fluids for growth factor activity, involvement with dedication of lineages, or the like.

The isolated c-kit positive fetal stem cells may be cryopreserved, i.e. frozen at liquid nitrogen temperatures and stored for long periods of time, being thawed and capable of being reused. The cells will usually be stored in 5% DMSO and 95% fetal calf serum. Once thawed, the cells may be expanded by use of growth factors or stromal cells associated with stem cell proliferation and differentiation.

The present invention contemplates also cryopreservation of the chorionic villus and amniotic fluid samples as well as the placenta samples, wherein once thawed, c-kit positive cells can be obtained.

For illustration purposes, c-kit$^{pos}$ cells were induced to different lineages as described in the Example. The ability to induce specific differentiation was initially evident by morphological changes, and was confirmed by immunocytochemical and gene expression analyses. Generally, the c-kit positive fetal stem cells can be differentiated into different cell lineages according to methods well known to one skilled in the art (Stem Cells: Scientific Progress and Future Research Directions. Appendix D. Department of Health and Human Services. June 2001. http://www.nih.gov/news/stemcell/scireport.ht).

Adipogenic specific chemical staining showed that it was possible to induce lipid accumulation in more than 95% of the c-kit$^{pos}$ chorionic villus cells when the cells were cultured in specific conditions. Adipocyte induction was confirmed with ppar$\gamma$2 and LPL expression at different time points.

Consistent with bone differentiation, chorionic and amniotic fetal stem cells showed to be able to produce alkaline phosphatase and to deposit calcium, and the values of both were higher than those reached by adult stem cells under the same conditions. Furthermore, c-kit$^{pos}$ cells in osteogenic media expressed specific genes implicated in mammalian bone development. Core binding factor A1 (Cbfa1) is an osteoblast specific transcription factor. Cbfa1 regulates the function of genes expressed in osteoblasts and encodes structural proteins of the bone extracellular matrix. Forced expression of Cbfa1 in non-osteoblastic cells leads to osteoblast-specific gene expression. Cbfa1 deficient mice and deletion or mutation of the same gene in humans causes cleidocranial dysplasia.

In postnatal life, growth and repair of skeletal muscle are mediated by a resident population of mononuclear myogenic precursors (the "satellite cells"); however their self-renewal potential is limited and decreases with age. Previous studies have shown that muscle cells can be derived from mesenchymal stem cells from bone marrow and peripheral tissue. It has been shown here that c-kit$^{pos}$ chorionic villus and amniotic cells can be induced towards muscle differentiation. The c-kit$^{pos}$ cells formed multinucleated cells that were positive for muscle differentiation markers (Desmin and Sarcomeric Tropomyosin). Furthermore by RT-PCR analysis, a characteristic pattern of gene expression, reflecting that seen with embryonic muscle development, was demonstrated. Previous studies in mouse embryos have shown that Myf6 is expressed transiently between days 9 and 11. In our study Myf6 was expressed at day 8 and suppressed at day 16. Myf5 in embryonic mouse development is expressed early and continues to be expressed until very late time points. In our study a low expression of Myf5 was detected in the induced cells throughout the experiment. Also, as has been shown with ES cells, MyoD expression was detectable at 8 days in the c-kit$^{pos}$ cells grown under myogenic conditions. Our findings illustrate that cells derived from chorionic villus, amniotic fluid and placenta can be induced towards muscle differentiation.

Endothelial cells are usually difficult to isolate and maintain in culture. P1H12, FVIII and KDR are specific markers of endothelial differentiation. Amniotic c-kit$^{pos}$ cells cultured in defined media were able to form fully differentiated endothelial cells that expressed specific markers.

In accordance with the present invention, fetal stem cells are obtained from human chorionic villus, amniotic fluid and placenta. Large quantities of chorionic villus, amniotic fluid and placenta cells can be obtained from subjects during pregnancy and/or at birth depending on which cell source is used. Fetal stem cells obtained from these sources may be cultured in various media, such as DMEM, F-12, M1 99, RPMI and combinations thereof, supplemented with fetal bovine serum (FBS), whole human serum (WHS), or supplemented with growth factors, cytokines, hormones, vitamins, antibiotics, or any combination thereof. DMEM media is preferred.

The fetal stem cells may also be expanded in the presence of an agent which suppresses cellular differentiation. Such agents are well-known in the art (Dushnik-Levinson, M. et al., "Embryogenesis in vitro: Study of Differentiation of Embryonic Stem Cells," Biol. Neonate, Vol. 67, 77-83, 1995). Examples of agents which suppress cellular differentiation include leukemia inhibitory factor (LIF) and stem cell factor. On the other hand, agents such as hydrocortisone, $Ca^{2+}$, keratinocyte growth factor (KGF), TGF-P, retinoic acid, insulin, prolactin, sodium butyrate, TPA, DIVISO, NMF, DMF, collagen, laminin, heparan SO4, androgen, estrogen, and combinations thereof may be used to induce differentiation (Culture of Epithelial Cells, (R. Ian Freshney ed., Wiley-Liss 1992)).

The cells may be assessed for viability, proliferation potential, and longevity using standard techniques in the art. For example, a trypanblue exclusion assay, a fluorescein diacetate uptake assay, a propidium iodide uptake assay, or other techniques known in the art may be used to assess viability. A thymidine uptake assay, an MTT cell proliferation assay, or other techniques known in the art may be used to assess proliferation. Longevity may be determined by the maximum number of population doublings in extended cultures or other techniques known in the art.

Additionally, cells of different lineages may be derived by inducing differentiation of fetal stem cells and as evidenced by changes in cellular antigens. Various differentiation-inducing agents are used to accomplish such differentiation, such as growth factors (for example EGF, aFGF, bFGF, PIDGF, TGF-P), hormones (including but not limited to insulin, triiodothyronine, hydrocortisone, and dexamethasone), cytokines (for example IL-1α or P, IFN-γ, TFN), matrix elements (for example collagen, laminin, heparan sulfate, Matrigel), retinoic acid, transferrin, TPA, and DMSO. Such differentiation-inducing agents are known to those of ordinary skill in the art (Culture of Epithelial Cells, (R. Ian Freshney ed., Wiley-Liss 1992)). Examples below describe differentiation of fetal stem cells into osteogenic, adipogenic, myogenic and endothelial lineages. Identification of differentiated cells may be accomplished by staining the cells with tissue-specific antibodies according to techniques known in the art.

In contrast to human embryonic stem (ES) cells whose use has raised ethical concerns, human fetal stem cells of the present invention are derived from a readily available source (chorionic villus or amniotic fluid or placenta) which is normally discarded after birth. Thus, cultured human fetal stem cells are ideal for use in regenerative and/or reconstructive surgery, as well as for use in gene therapy. Some specific applications of human fetal stem cells are described below.

Fetal stem cells may be used in autologous/heterologous enzyme replacement therapy in specific conditions including, but not limited to, lysosomal storage diseases, such as Tay-Sachs, Niemann-Pick, Fabry's, Gaucher's, Hunter's, Hurler's syndrome, as well as other gangliosidoses, mucopolysaccharidoses, and glycogenoses.

Additionally, the fetal stem cells of the present invention may be used as autologous/heterologous transgene carriers in gene therapy to correct inborn errors of metabolism affecting the cardiovascular, respiratory, gastrointestinal, reproductive, and nervous systems, or to treat cancer and other pathological conditions.

Fetal stem cells of the present invention can be used in autologous/heterologous tissue regeneration/replacement therapy, including but not limited to treatment of corneal epithelial defects, cartilage repair, facial dermabrasion, burn and wound dressing for traumatic injuries of skin, mucosal membranes, tympanic membranes, intestinal linings, and neurological structures. For example, augmentation of myocardial performance can be achieved by the transplantation of exogenous fetal stem cells into damaged myocardium, a procedure known as cellular cardiomyoplasty (CCM) which can be used for enhancing myocardial performance and treating end-stage cardiac disease. Fetal stem cells according to the present invention can also be used as a tool for the repair of a number of CNS disorders as described in a review by Cao et al. (Stem cell repair of central nervous system injury, J. Neuroscience Res. 68:501-510, 2002).

Fetal stem cells of the present invention can also be used in reconstructive treatment of damaged tissue by surgical implantation of cell sheets, disaggregated cells, and cells embedded in carriers for regeneration of tissues for which differentiated cells have been produced. The cells may also be used in tissue engineered constructs. Such constructs comprise a biocompatible polymer formed into a scaffold suitable for cell growth. The scaffold can be shaped into a heat valve, vessel (tubular), planar construct or any other suitable shape. Such constructs are well known in the art (see, e.g., WO02/035992, U.S. Pat. Nos. 6,479,064, 6,461,628).

The amniotic fluid, chorionic villus, placenta tissue and fetal stem cells, before or after differentiation, may be cryopreserved in a cryoprotective solution comprising a medium or buffer and a cryoprotective agent. Examples of media are Dulbecco's Modified Eagle Medium (DMEM), Medium 199 (M199), F-12 Medium, and RPMI Medium. An example of a buffer is phosphate buffered saline (PBS). Examples of cryoprotective agents are dimethylsulfoxide (DMSO) and glycerol. Examples of cryoprotective solutions are: DMEM/glycerol (1:1), DMEM/7.5% DMSO, M199/7.5% DMSO, and PBS/3.5 M DMSO. Optionally, the samples may be treated with antibiotics such as penicillin or streptomycin prior to cryopreservation. Cryopreservation may be accomplished using a rapid, flash-freeze method or by more conventional controlled rate-freeze methods. Rapid freezing of amniotic tissue may be accomplished by placing sample(s) in a freezing tube containing a cryoprotective solution and then rapidly immersing the freezing tube in liquid nitrogen. General slow freezing may be accomplished by placing sample(s) in a freezing tube containing a cryoprotective solution and then placing the freezing tube in a −70° C. freezer. Alternatively, the sample(s) may be subjected to controlled rate freezing using a standard cryogenic rate controlled system.

Products of fetal stem cells of the present invention may be used in reconstructive treatment, either in vivo or ex vivo. Examples of agents that can be produced using fetal stem cells of the present invention include growth factors, cytokines, and other biological response modifiers.

The references cited herein and throughout the specification are incorporated by reference in their entirety.

The invention will be further clarified by the following examples, which are intended to be purely exemplary of the invention.

EXAMPLES

In this example the feasibility of isolating stem cells from human embryonic and fetal chorionic villi and amniotic fluid was investigated. Discarded cultures of chorionic villi cells and human amniotic fluid cells collected for prenatal diagnostic tests were obtained from more than 300 human pregnant females ranging from 23 to 42 years of age under an approved institutional Investigation Review Board protocol.

To establish the cultures, human amniotic fluid was obtained by transabdominal amniocentesis at 14 to 21 weeks of gestation, and human embryonic chorionic villus tissue specimens were obtained at 10 to 12 weeks of gestation through a transabdominal approach.

Amniotic fluid samples were centrifuged and the cell supernatant was resuspended in culture medium. Approximately $10^4$ cells were seeded on 22×22 mm cover slips. Cultures were grown to confluence for about 3 to 4 weeks in 5% $CO_2$ at 37° C. Fresh medium was applied after five days of culture and every third day thereafter.

Chorionic villus cells were isolated from single villus under light microscopy. The cells were allowed to proliferate in vitro and were maintained in culture for about 4 weeks. The culture medium consisted of modified αMEM (18% Chang Medium B, 2% Chang C with 15% embryonic stem cell-certified fetal bovine serum, antibiotics and L-glutamine) (J. H. Priest, *Prenatal Chromosomal Diagnosis and Cell Culture* in *The ACT Cytogenetics Laboratory Manual*, Margaret J. Barch (Raven Press, New York ed. 2, 1991) cap. 5 p. 149).

The cells were sub-cultured using 0.25% trypsin containing 1 mM EDTA for 5 minutes at 37° C. Cells were seeded at 3000 cells/cm² in 24 well plates. Cell numbers were determined after 4, 8, 16, 24 and 32 days in quadruplicate values. For the first time point (4 days), the medium was removed from the 24 well plates. The cells were rinsed once with PBS/EDTA, and were incubated with 0.2 ml trypsin/EDTA for 10 minutes at 37° C. The cells were resuspended with trypsin/EDTA solution several times to avoid cell clusters, before being transferred to 9.8 ml of isotonic fluid. Cells were counted as recommended by the manufacturer's instructions (Coulter Counter). An MTT assay was performed after 4, 8, 16, 24 and 32 days. 100 μl of MTT reagent (Sigma-Aldrich) was added to 1 ml of medium for 3 hours. The cells were lysed and color was extracted with isopropanal containing 0.1M HCl. Extinction was read in a Biorad reader at 570 nm against 655 nm. Results were expressed as a cell count. Growth curves from both cell sources were obtained and the morphology of the cells in culture was documented.

Cells from chorionic villi and amniotic fluid underwent phenotypic analysis. Immunocytochemistry of the amniotic fluid confirmed that most of the cells were of epithelial origin and stained positively for cytokeratins. Most of the stromal cells stained for α-actin, and only a few cells were positive for desmin or myosin expression (von Koskull, H., et al., Prenat. Diagn., 1(4), p. 259 (1981); Medina-Gomez, P. and T. H. Johnston, Hum. Genet., 60(4), p. 310 (1982)).

The cells were analyzed using FACS for CD34 (Pharmingen International, San Diego, Calif.), CD90 (Santa Cruz Biotechnology, Inc., Santa Cruz, Calif.), CD105 (Pharningen International), CD133 (Miltenyi Biotec, Bergisch Gladbach, Germany), and c-kit (Santa Cruz Biotechnology, Inc). For all antibodies, $0.5 \times 10^6$ of either chorionic villus or amniotic cells were incubated in 500 μl of primary antibody solution (2% FBS in PBS) at a concentration of 1:100 on ice for 30 minutes. After incubation with the primary antibodies, the cells were washed twice with 2 ml of 2% FBS in PBS, spun down at 1100 RPM for 7 minutes, and either resuspended in 0.5 ml PBS containing 2% FBS, or incubated in the dark, on ice for 30 minutes, in 100 μl of FITC labeled secondary antibody (1:100, Southern Biotechnology Associates Inc., Birmingham, Ala.). The cells were washed twice with 2 ml of PBS containing 2% FBS, spun down, and resuspended in PBS with 2% FBS for cell analysis. IgG-PE (Pharmingen International) and IgG1κ (unconjugated, Pharmingen International) were used as controls. FACS analysis was performed with a FACScalibur (Becton Dickinson, San Jose, Calif.). Immunocytochemistry was done as follow: cells, grown on chamber slides (Nalge Nunc Int., Naperville, Ill.), were fixed in 4% formaldehyde and in ice-cold methanol. Cell layers were washed with PBS. Cell surface gly-colipid- and glycoprotein-specific mAbs were used at 1:15 to 1:50 dilution. MC480 (SSEA-1), MC631 (SSEA-3), and MC813-70 (SSEA-4) antibodies were supplied by the Developmental Studies Hybridoma Bank (University of Iowa, Iowa City). Antibodies were detected using biotinylated anti-mouse secondary antibody, strepavi-din-conjugated horseradish peroxidase, and 3-amino-9-ethylcarbazole chromagen (BioGenex). Cells prepared for cytogenetic analysis were incubated in growth media with 0.1 mg/ml of Colcemid for 3-4 hr, trypsinized, resuspended in 0.075 M KCl, and incubated for 20 min at 37° C., then fixed in 3:1 methanolyacetic acid.

FACS analyses of the cells showed that between 18% and 21% of the cells expressed CD90 and CD105, while much lower percentages of cells expressed c-kit, CD34 and AC133 (between 0.8% and 3%). Similar patterns of expression were obtained for the chorionic villus cells.

Figure 1B:
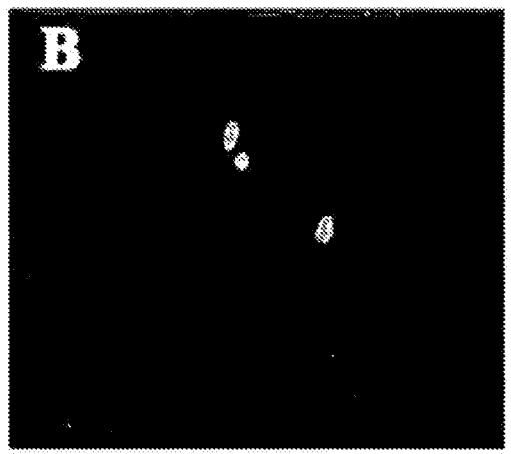
Figure 1C:
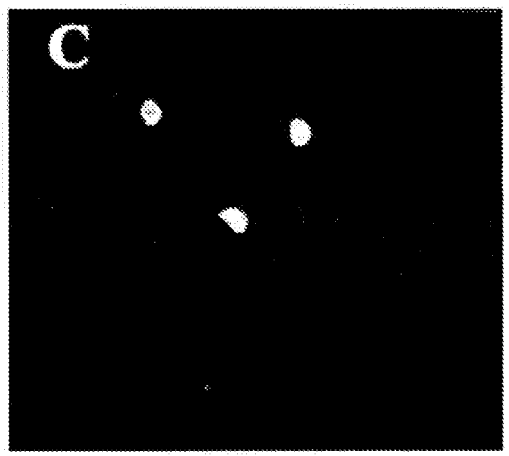
Figure 1D:
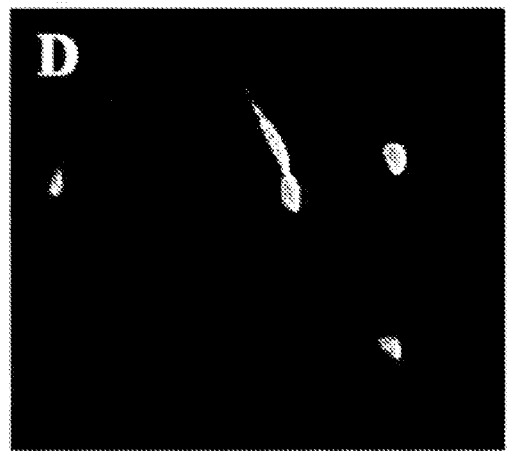

Cells expressing c-kit (c-kit$^{pos}$) were successfully immuno-isolated from chorionic villi and were maintained in culture in Chang medium. The c-kit$^{pos}$ cells expressed human embryonic stage specific markers SSAE3 and SSAE4 and did not express mouse embryonic stage specific marker SSAE1 (FIG. 1B-D) (Thomson, J. A., et al., Science, 282(5391), p. 1145 (1998)). The c-kit$^{pos}$ cells maintained a round shape when they were cultured in non-treated culture dishes for almost one week and their proliferative activity was low. After the first week, the cells begun to adhere to the plates and changed their morphology, becoming more elongated, and proliferating more rapidly. Interestingly and importantly, no feeder layers were required either for maintenance or expansion.

In this study c-kit$^{pos}$ cells, obtained from early to late passages, were inducible to different cell lineages including osteogenic, adipogenic, myogenic, neurogenic and endothelial cell lineages under specific growth factors. The ability to induce specific differentiation was initially evident by morphological changes, and was also confirmed immunocytochemically, by gene expression patterns, and by cell-specific functional analyses.

Stem cells from bone marrow were purchased (Clonetics) and used as a positive control. The CD34, CD90, CD105 and AC133 immunoisolated cells, and the remaining non-immunoseparated cells did not show any pluripotential capacity. Because amniotic fluid contains both urine and peritoneal fluid, cells isolated from discarded human neonatal urine and peritoneal fluid were used as controls. Human urine and peritoneal control fluids did not yield any c-kit$^{pos}$ cells, and the c-kit$^{neg}$ cells did not show any pluripotential ability.

It is known that amniotic fluid, in general, contains very few maternal cells. To determine if any maternal c-kit$^{pos}$ cells were present in the chorionic villus or amniotic fluid samples, studies were performed using cells from male fetuses. All the caryotyped c-kit$^{pos}$ cells showed an XY karyotype indicating that no C-kit$^{pos}$ maternal cells were present in the studies samples. C-kit$^{pos}$ cells from female embryos and fetuses were used as controls, and they did not show any difference in their pluripotential ability.

Figure 1E:
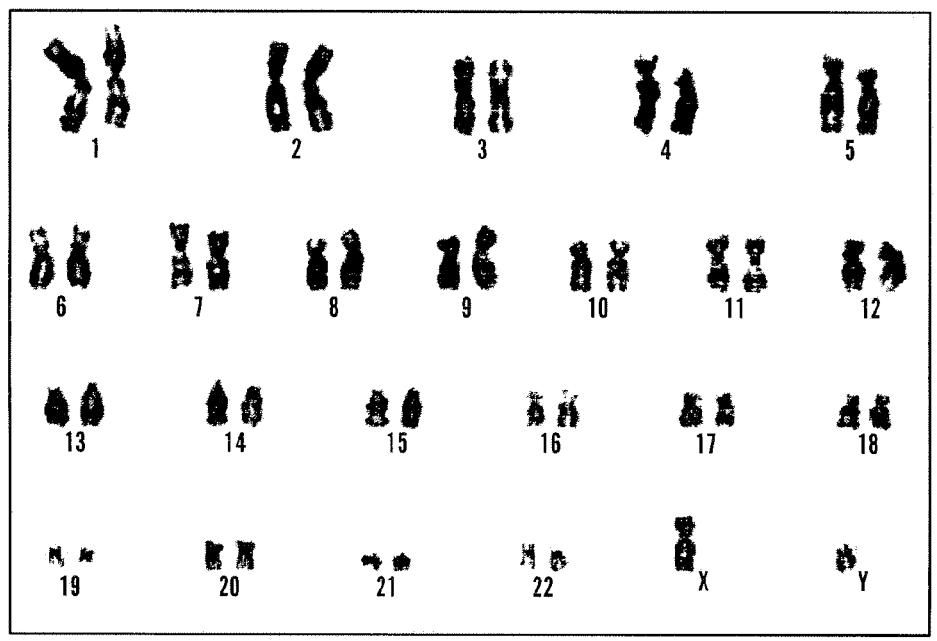

The c-kit$^{pos}$ cells derived from chorionic villi and amniotic fluid showed a high self-renewal capacity with over 250 population doublings, far exceeding Hayflick's limit. The cells have now been continuously passaged for over 18 months and they have maintained their undifferentiated state. We have also demonstrated that late passage c-kit$^{pos}$ cells maintain their pluripotential capacity and a normal karyotype after 250 population doublings (FIG. 1E).

Figure 1F:
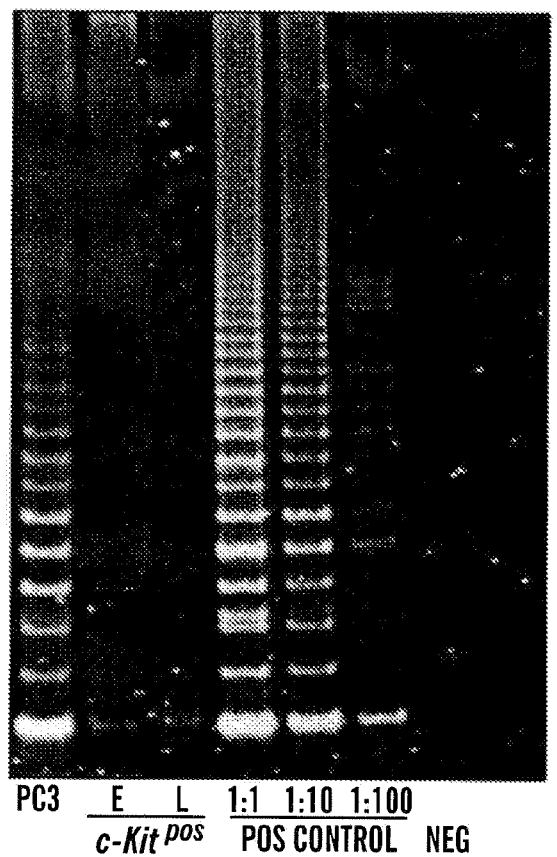
Figure 1G:
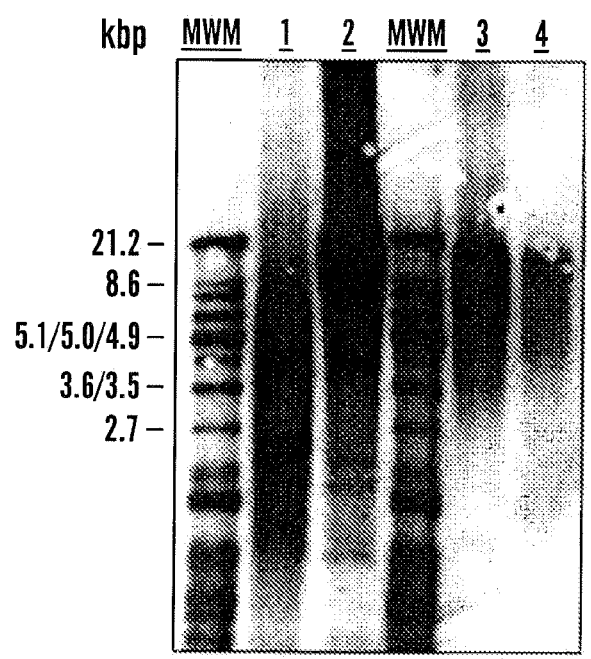

Telomerase activity is normally detectable in human germ cells (Thomson, J. A., et al., Science, 282(5391), p. 1145 (1998)), most immortalized cell lines, and 80-90% of human tumor samples, in which the telomere length is preserved. We evaluated the telomerase activity in the isolated and cultured c-kit$^{pos}$ cells using the Telomerase Repeat Amplification Protocol (TRAP) assay (FIG. 1F). TRAP analysis (TRAPeze kit, Intergenco Pharmaceuticals) was performed as described in the manufacturer's protocol with one modification. CHAP's lysates were subjected to 36 cycles of PCR amplification after the telomerase extension step. Low telomerase activity was detected with the TRAP-assay in the amniotic c-kit$^{pos}$ cells (lane 1) compared to the control (lanes 3 and 4). However, after differentiation, the c-kit$^{pos}$ cells did not show any telomerase activity (lane 2). To confirm that the measured telomerase activity was of functional relevance to the isolated cells, the telomere length of the c-kit$^{pos}$ cells at early and late passages were determined by terminal restriction fragment (TRF) analyses. Total cellular DNA was isolated by the DNeasy Tissue Kit (Qiagen Corp) and 2 µg was used for Southern Blot analysis of TRF lengths (TeloTAGGG Telomere Length Assay, Roche Molecular) as described in the manufacturer's protocol. Briefly, purified genomic DNA was digested with a mixture of frequently cutting restriction enzymes. The resulting fragments were agarose gel electrophoresed and transferred to a nylon membrane by Southern blotting. Hybridization to a digoxigenin (DIG)-labeled probe specific for the telomeric repeats was followed by chemiluminescent detection and exposure of the membrane to autoradiography film. TRF qualitative analysis demonstrated that the c-kit$^{pos}$ cells had similar telomere lengths, both at early (mean TRF length approximately 20 kb) and late (mean TRF length approximately 20 kb) passages (FIG. 1G).

However C-kit$^{pos}$ cells derived from chorionic villi and amniotic fluid expanded clonally more than 250 population doublings while maintaining approximately the same telomere length and had additionally acquired telomerase activity. This phenomenon suggests that the cell population could have an alternative mechanism for lengthening telomeres (ALT) (16, 17). One possible answer could be derived from the clonal fluctuations. Some tested clones could have been overlengthned by the action of telomere-lengthening by an unknown mechanism. Regulation factors could therefore influence the activation and inactivation of the telomerase without influencing the telomere length (Brayan, T. M et al (1998) Telomere length dynamics in telomerase-positive immortal human cell population). The explanation of this particular phenomenon is not clear and the mechanism for the longevity of these cells in culture is unknown.

To prove the capacity of the c-kit$^{pos}$ cells isolated from amniotic fluid and chorionic villi to differentiate into various cell lineages we used a method of retroviral marling. CKit$^{pos}$ cells were transduced with a puc-CMMP-IC-eGFP retrovirus and expanded. The infected-cKit$^{pos}$ were sorted by FACS-Excalibur and single eGFP$^+$-cells were plated per well in a 96 wells-plate and expanded. The derived clones were sorted one more time by FACScan instrument (Becton Dickinson, San Jose, Calif.) in-line with a Power Macintosh computer using the CELLQuest software in order to obtain a subpopulation of clones. The DNA from the original clones and derived subclones was extracted using a Dnaesy Tissue Kit (Qiagen) and the concentration was measured with a Spectrofotometer (Spectronic 601). Three samples of genomic DNA for each clone and subclone were digest for three hours with a different mix of restriction enzymes (mix1. SapI, MfeI, HpaI, DraIII; mix2. BamHI, NheI, HindIII, XhoI, PacI; mix3. BglII, AseI). The fragments were separated by electrophoresis and transfer by capillarity to a naylon membrane. An eGFP-cDNA probe was constructed from a plasmid (PEGFP-N1 . . . ) digesting the plasmid with AgeI and NotI. The fragment was separated by electrophoresis and the digested DNA was extract with a Gel Extraction Kit (Qiagen) and labelled with digoxigenin for detection with alkaline phosphatase metabolising CDP-Star, a highly sensitive chemiluminescence substrate (DIG High Prime DNA Labeling and Detection Starter Kit II, Roche). The blotted DNA fragments were hybridised to the Dig-labelled eGFP cDNA probe and the retrovirus insertion was determined by detection exposing the membrane to X-ray film.

All experiments were performed with c-kit$^{pos}$ cells obtained from twelve clonal cell populations, according to their gestational age (10, 11, 12, 13, 14, 15, 16, 17, 18, 19, 20 and 21 weeks). Furthermore, all experiments were also performed with five single c-kit$^{pos}$ clonal cell populations obtained from a single fetus (11, 14, 16, 18 and 20 weeks of gestation). Cells from the different clones showed a similar morphology and growth behavior. Cells from all clones underwent osteogenic, adipogenic, myogenic, neurogenic and endothelial differentiation. No statistical differences were noted in the ability of the 17 clonal cell populations to differentiate into separate lineages.

Osteogenic induction. For the induction of osteogenic differentiation, c-kit$^{pos}$ cells isolated from amniotic fluid and chorionic villi were cultured in a defined osteogenic medium. For the induction of osteogenic differentiation, the cells were seeded at a density of 3000 cells/cm$^2$ and were cultured in DMEM low glucose medium (Gibco/Brl) with 10% fetal bovine serum (FBS, Gibco/Brl), 1% antibiotics (Gibco/Brl), and osteogenic supplements [100 nM dexamethasone (Sigma-Aldrich), 10 mM beta-glycerophosphate (Sigma-Aldrich), and 0.05 mM ascorbic acid-2-phosphate (Wako Chemicals, Irving, Tex.)]. Jaiswal, N., et al., J. Cell. Biochem., 64(2), p. 295 (1997).

Figure 2A:
Figure 2B:
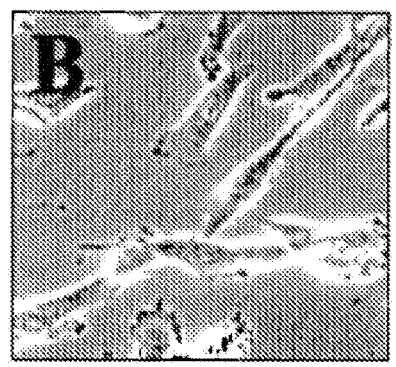

Control medium was essentially modified αMEM. Medium was changed about every 3 days. Light microscopy analysis of the cells showed that, within 4 days in the osteogenic medium, c-kit$^{pos}$ cells lost their spindle shape phenotype (FIG. 2A) and developed an osteoblastic-like appearance with fingerlike excavations into the cytoplasm (FIG. 2B). At day 16, the cells aggregated, showing typical lamellar bone-like structures. Consistent with bone differentiation, the c-kit$^{pos}$ cells cultured under osteogenesis inducing conditions produced alkaline phosphatase (AP) and showed calcium deposits. Interestingly, both the amount of AP production and calcium deposition was higher than those reached by adult osteogenic stem cells cultured under the same conditions. AP activity was measured using a quantitative assay for p-Nitrophenyl, which is equivalent to AP production. Alkaline phosphatase enzyme cell activity was measured in quadruplicate cultures. After rinsing with PBS, the cells were incubated with 2-amino-2-methyl-1-propanol buffer, pH 10.3 (Sigma-Aldrich #221/26) with 40 mg p-nitrophenyl phosphate (Sigma-Aldrich #104/40) added, at 37° C. for 3 to 35 min. AP activity was calculated after measuring the absorbance of p-nitrophenyl products formed at 405 nm on a micro plate reader (Molecular Devices, Spectra Max Plus). As a standard, p-nitrophenyl standard solution (Sigma-Aldrich #104-1) diluted in 2-amino-2-methyl-1-propanol buffer in concentrations from 0 to 100 nMol p-nitrophenyl was used. Enzyme activity was expressed as nMol p-Nitrophenyl/min/$10^6$ cells.

Histochemical Analyses. Alkaline phosphatase activity was determined histologically in cells according to the manufacturer's instructions (Sigma-Aldrich Kit #85). Briefly, cells were fixed in a citrate-acetone solution. An alkaline-dye mixture (fast blue RR solution with naphthol AS-MX phosphate alkaline solution) was added to the cells in the 35 mm culture dishes. The cell cultures were protected from direct light. Prior to viewing, the cell cultures were rinsed with deionized water and air-dried. AP production in the c-kit$^{pos}$ cells grown in osteogenic-inducing medium increased by a factor of 250 compared to c-kit$^{pos}$ cells grown in control medium and c-kit$^{neg}$ cells grown in osteogenic medium at days 16 and 24 (FIG. 2C).

A major feature of osteogenic differentiation is the ability of the cells to precipitate calcium. Cell associated mineralization may be analyzed using von Kossa staining and by measuring calcium content in the cells in culture. Von Kossa staining of cells grown in the osteogenic medium showed enhanced silver nitrate precipitation by day 16, indicating high levels of calcium. The presence of mineralization in cell culture was determined by von Kossa staining. The cell culture plates were fixed with 10% formaldehyde for 1 h, incubated with 2% silver nitrate solution for 10 min in the dark, washed thoroughly with deionized water, and then exposed to UV-light for 15 min. Calcium content continued to increase exponentially at 24 and 32 days. In contrast, cells in the control medium did not show any silver nitrate precipitation (FIG. 2G).

Calcium deposition by the cells was also measured with a quantitative chemical assay which measures calcium-cresolophthalein complexes. Cells undergoing osteogenic induction showed a significant increase in calcium precipitation after 16 days (up to 4 mg/dl). The precipitation of calcium increased up to 70 mg/dl at 32 days. In contrast, cells grown in the control medium did not show any increase in calcium precipitation (1.6 mg/dl) by day 32 (FIGS. 2H and I).

Figure 2C:
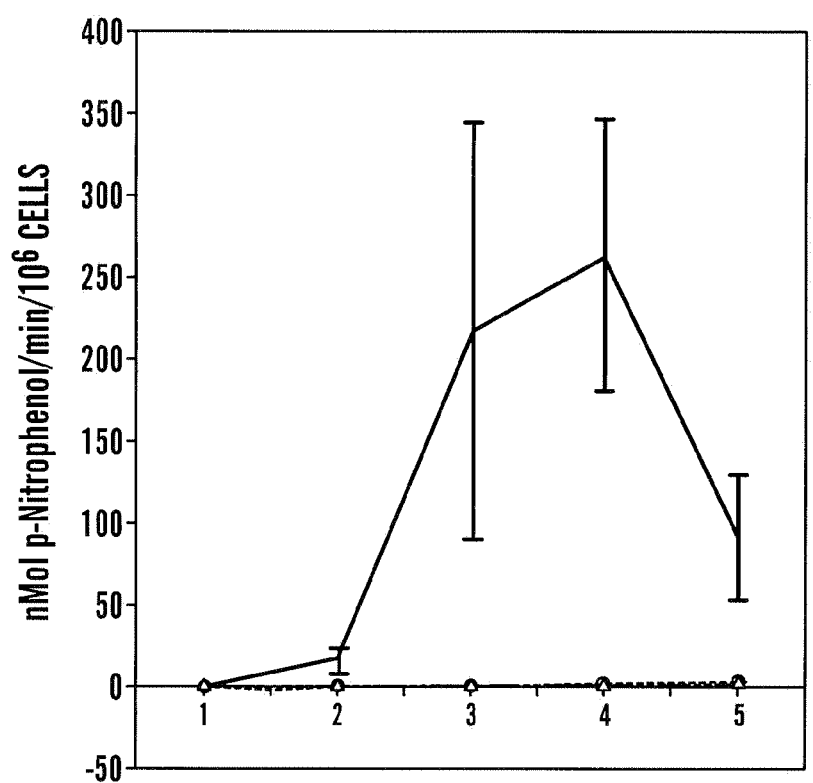
Figure 2G:
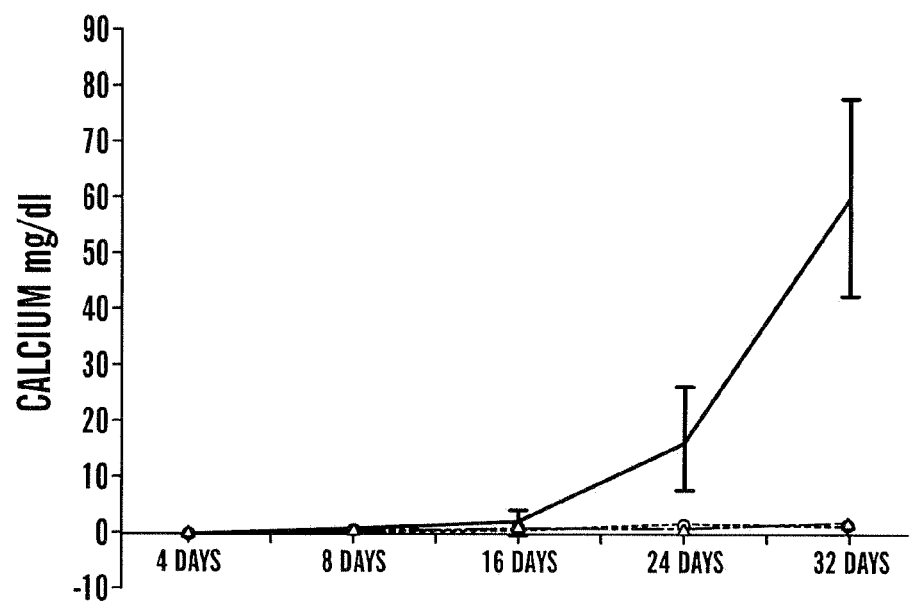
Figure 2H:
Figure 2I:
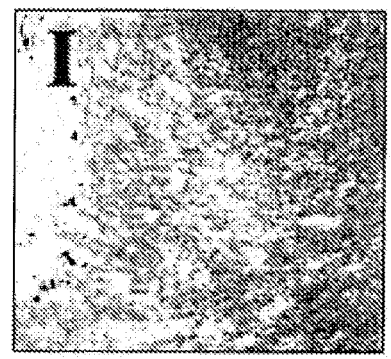
Figure 2J:
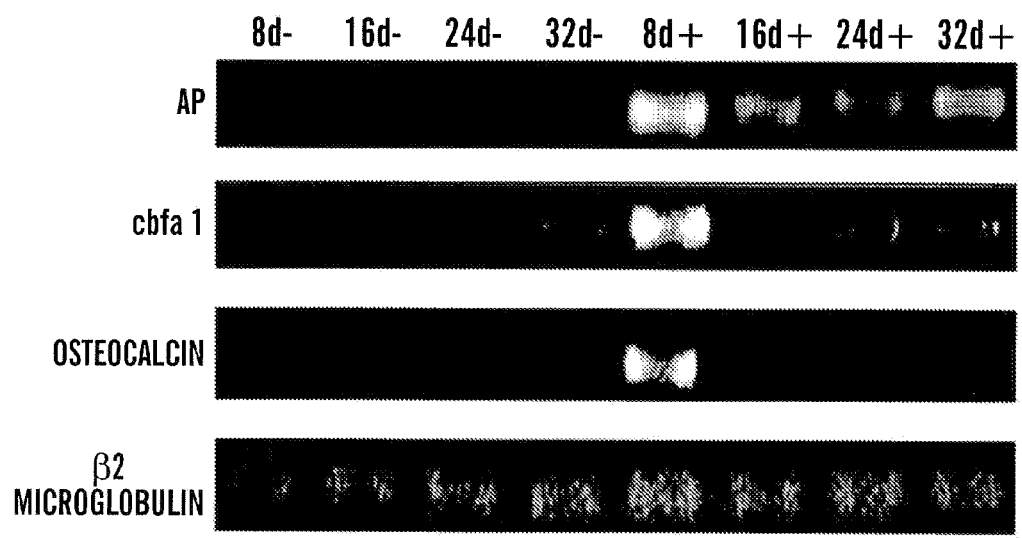

C-kit$^{pos}$ cells in osteogenic medium expressed specific genes implicated in mammalian bone development (AP, core binding factor A1 (cbfa1), and osteocalcin) (FIG. 2C). RNA was isolated from cultured cells and cell pellets with RNAzol reagent (Tel-Test Inc., Friendswood, Tex.) according to the manufacturer's protocol. RNA (2 µg) was processed for c-DNA synthesis with Superscript II reverse transcriptase with random hexamers (Life Technologies). C-DNA was used for each PCR reaction, in a final volume of 30 µl with 200 nM dNTP, 10 pM of each primer, 0.3 U Taq-DNA-polymerase, reaction buffer, and MgCl2 (Life Technologies), in a PTC-100 cycler (MJ-Research Inc., Watertown, Mass.). The cycling conditions consisted of 94° C. for 2 minutes, annealing at 63° C. for 40 seconds, and elongation at 72° C. for 1 minute. Cycle numbers varied between 22 and 37 cycles and were chosen in the exponential phase of the RT-PCR reaction. Primer sequences and fragment sizes are listed in Table 1. All primers were obtained from Life Technologies. Primers for human core binding factor A1 (cbfa1) primers (sense 5'GGCCTTCCACTCTCAGTAAGA3' (SEQ ID NO:1) and antisense 5'GATTCATCCATTCTGCCACTA3', (SEQ ID NO:2)28 cycles at 63° C.) amplified a fragment of 474 bp and human osteocalcin (sense 5'CCCTCACACTC-CTCGCCCTAT3' (SEQ ID NO:3) and antisense 5'GGTAGCGCCTGGGTCTCTTCA3', SEQ ID NO:4) amplified a fragment of 144 bp. Human peroxisome proliferator-activated receptor γ2 (pparγ2) primers (sense 5'TGAACGACCAAGTAACTCTCC3' (SEQ ID NO:5) and antisense 5' CTCATGTCTGTCTCCGTCTTC3', (SEQ ID NO:6) 29 cycles at 64° C.) yielded a fragment of 460 bp. 533 bp. Human lipoprotein lipase (lpl) primers (sense 5'CTG-GTCGAAGCATTGGAAT3' (SEQ ID NO:7) and antisense 5'TGTAGGGCATCTGAGAACGAG3', (SEQ ID NO:8) 29 cycles at 64° C.) amplified a fragment of 366 bp. Human Myogenic Regulatory Factor 4 (MRF4) (sense 5'CGACAG-CAGCGGAGAGG3' (SEQ ID NO:9) and antisense 5'GGAATGATCGGAAACACTTGG3', (SEQ ID NO:10) 37 cycles at 62° C.) was detected as band of 421 bp and human myoD (sense TCCGCGACGTAGACCTGAC3' (SEQ ID NO:11) and antisense 5'GATATAGCGGATGGCGTTGC3', SEQ ID NO:12) amplified a segment of 449 bp. Human desmin primers (sense 5'CCATCGCGGCTAAGAACATT3' (SEQ ID NO:13) and antisense 5'TCGGAAGT-TGAGGGCAGAGTA3', (SEQ ID NO:14) 27 cycles at 62° C.) amplified a fragment of 440 bp, Primers for human β2-microglobulin (β2-MG) (sense 5'GCTCGCGCTACTCTCTC3' (SEQ ID NO:15) and antisense 5'TTAACTATCTTGGGCT-GTGAC3', (SEQ ID NO:16) 23-26 cycles at 62-64° C.) amplified a fragment of 315 bp. Primers for human CD106 (VCAM) (sense 5'TCCAGCGAGGGTCTACCAG3' (SEQ ID NO:16) antisense 5'TGTTTGCGTACTCTGCCTTTG3', SEQ ID NO:17) amplified a segment of 774 bp and human CD31 (PECAM) (sense 5'CCTTCTCTACACCCAAGT-TCC3' (SEQ ID NO:18) and antisense 5'GAAATAG-GCAAAGTTCCACTG3', SEQ ID NO:19) yielded a fragment of 628 bp.

C-kit$^{pos}$ cells grown in osteogenic medium showed an activation of the AP gene at each time point. No transcription of the AP gene was detected at 8, 16, 24 and 32 days in the c-kit$^{pos}$ cells grown in control medium. Expression of cbfa1, a transcription factor specifically expressed in osteoblasts and hypertrophic chondrocytes that regulates gene expression of structural proteins of the bone extracellular matrix in osteoblasts (24, 25), was highest in cells grown in osteogenic inducing medium at day 8 and decreased slightly at days 16, 24 and 32. The expression of cbfa1 in the controls was significantly lower at each time point. Osteocalcin was expressed only in the c-kit$^{pos}$ cells in osteogenic conditions at 8 days. No expression of osteocalcin was detected in the c-kit$^{pos}$ cells in the control medium and c-kit$^{neg}$ cells in osteogenic medium at any time point.

C-kit$^{pos}$ cells were also seeded on hydroxyapatite-collagen scaffolds (Collagraft, Neucoll, Zimmer, Warsaw, Indiana) at a density of 10×10$^6$ cells/cm$^2$. Cells were induced into an osteogenic lineage in a bioreactor for 16 d. The rods were implanted subcutaneously in athymic mice, harvested after 4 and 8 weeks, and analyzed. Bone-like tissue was evident, surrounded by an extracellular matrix which stained blue with Masson's trichrome. Toluidine blue staining confirmed the osteogenic phenotype. Small calcified areas within the implanted tissue stained positively with von Kossa, indicating bone formation. Unseeded constructs, as controls, showed only a few infiltrating cells, and no bone-like structures were noted (FIG. 2).

Adipogenic induction. To promote adipogenic differentiation, we cultured the c-kit$^{pos}$ cells in defined adipogenic medium. For the induction of adipogenic differentiation, the cells were seeded at a density of 3000 cells/cm$^2$ and were cultured in DMEM low glucose medium with 10% FBS, 1% antibiotics, and adipogenic supplements [1 μM dexamethasone, 1 mM 3-isobutyl-1-methylxanthine (Sigma-Aldrich), 10 μg/ml insulin (Sigma-Aldrich), and 60 μM indomethacin (Sigma-Aldrich)].

Figure 3A:
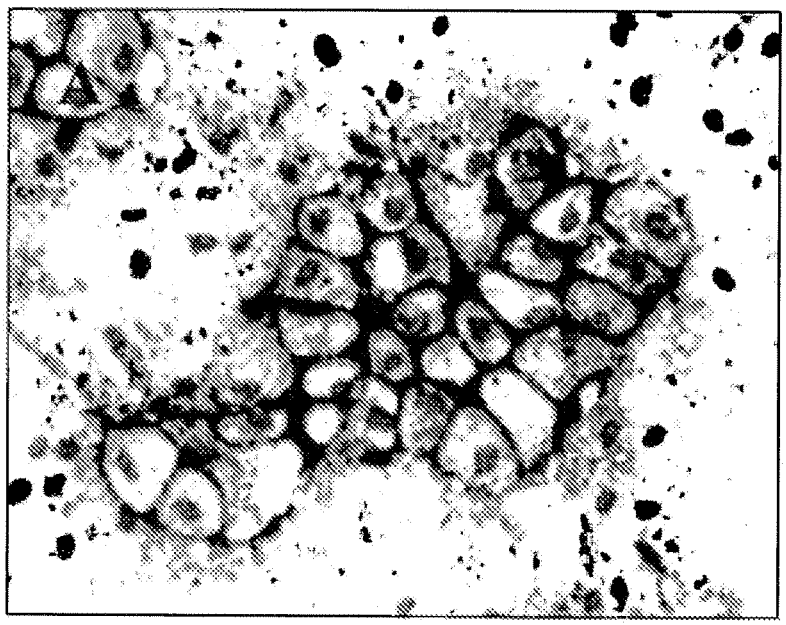
Figure 3B:
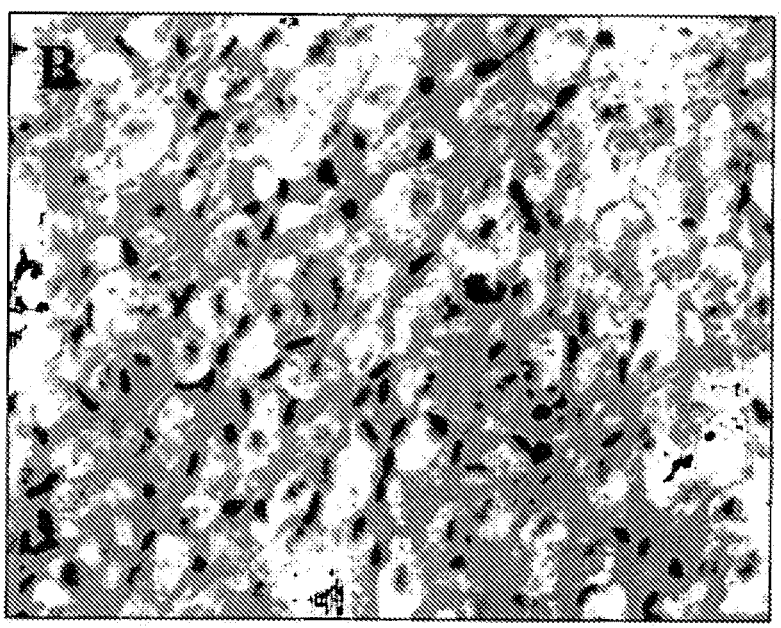

Control medium consisted of modified αMEM. Medium changes were performed every 3 days. C-kit$^{pos}$ cells cultured with adipogenic supplements changed their morphology from elongated to round within 8 days. This coincided with the accumulation of intracellular triglyceride droplets [FIG. 3A]. The presence of adipose elements in cell culture was determined with Oil-O-Red staining. The 2 well chamber slides were washed in deionized water and air-dried. The cells were incubated with oil red O staining solution for 15 minutes, rinsed with 50% ethanol 3 times, rinsed with distilled water, counterstained with Gills hematoxilin for 30 sec to 1 min, and rinsed in deionized water 3 to 4 times. After 16 days in culture, more than 95% of the cells had their cytoplasm filled with lipid-rich vacuoles, which stained with Oil-O-Red (FIG. 3B).

Figure 3C:
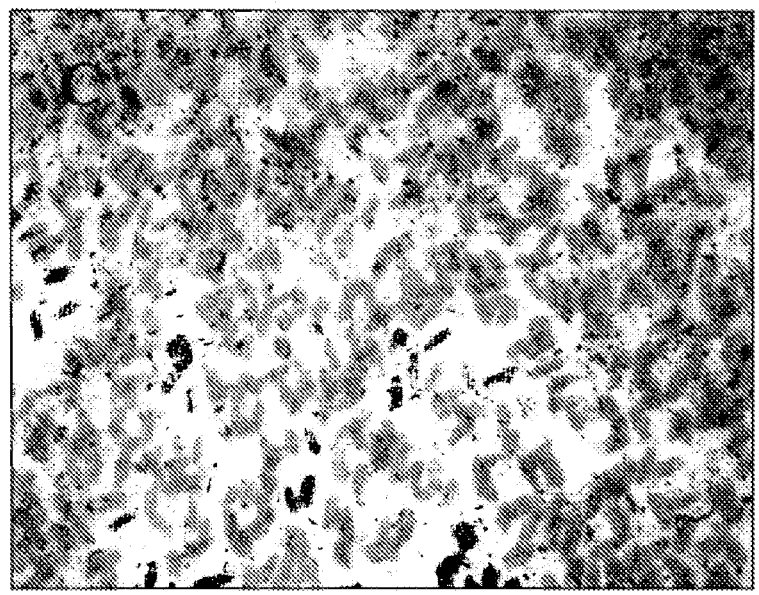
Figure 3D:
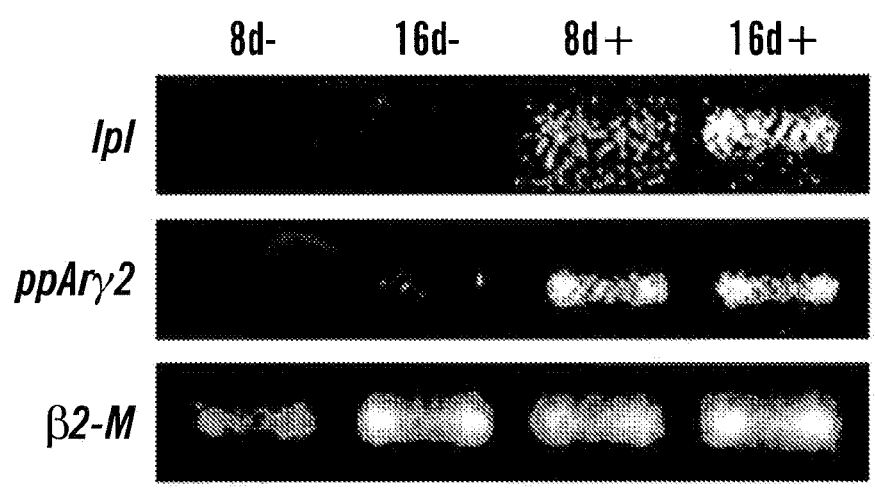

Chamber slides were mounted with water-based mounting media. The c-kit$^{pos}$ cells cultured in control medium and the c-kit$^{neg}$ cells cultured in adipogenic medium did not show any phenotypic changes consistent with adipogenic differentiation and did not stain with Oil-O-Red (FIG. 3C).

Adipogenic differentiation was confirmed by RT-PCR analysis. We analyzed the expression of peroxisome proliferation-activated receptor γ2 (pparγ2) (28, 29) a transcription factor that regulates adipogenesis, and of lipoprotein lipase. Expression of these genes was upregulated in the c-kit$^{pos}$ cells under adipogenic conditions. C-kit$^{pos}$ cells cultured under control conditions and c-kit$^{neg}$ cells cultured under adipogenic conditions did not express either gene at any time point [FIG. 3D].

C-kit$^{pos}$ cells were seeded on polyglycolic acid (PGA) polymer scaffolds at a density of 10×10$^6$ cells/cm$^2$. Cells were induced into an adipogenic lineage in a bioreactor for 16d. The scaffolds were implanted subcutaneously in athymic mice, harvested after 4 and 8 weeks, and analyzed. The retrieved scaffolds showed the formation of fatty tissues grossly. The presence of adipose tissue was confirmed with Oil-O-Red staining [FIG. 3].

Myogenic induction. In postnatal life, growth and repair of skeletal muscle are mediated by a resident population of mononuclear myogenic precursors (satellite cells); however their self-renewal potential is limited and decreases with age. Previous studies have shown that muscle cells can be derived from mesenchymal stem cells from bone marrow and peripheral tissue (30). In this study, c-kit$^{pos}$ cells were induced towards muscle differentiation. We seeded c-kit$^{pos}$ cells in 35 mm plates precoated with Matrigel in a defined medium. The defined myoblast growth medium consisted of DMEM low glucose containing 10% horse serum (GIBCO, BRL), 0.5% chick embryo extract (GIBCO, BRL) and 1% penicillin/streptomycin (GIBCO, BRL) (Reddel, R. R. et al., (1997). Immortalized cells with no detectable telomerase activity. Biochemistry 62, 1254-1262). Matrigel (Collaborative Biomedical Products, Universal Biologicals Ltd.) was diluted in DMEM to 1 mg/ml, plated and incubated for 1 h at 37° C., before the cells were seeded. Rosenblatt, J. D., et al., In Vitro Cell Dev. Biol. Anim., 31(10), p. 773 (1995). Defined medium containing 5-azacytidine was added after 12 hours and replaced 24 hours later with 5-azacytidine-free defined medium. As a control, undifferentiated cells were grown in 35 mm plates with modified αMEM. Medium changes were performed every 3 days.

Figure 4A:
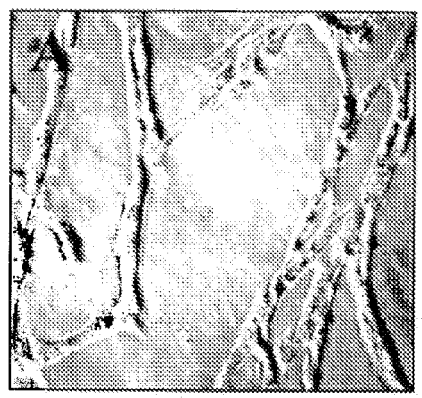
Figure 4B:
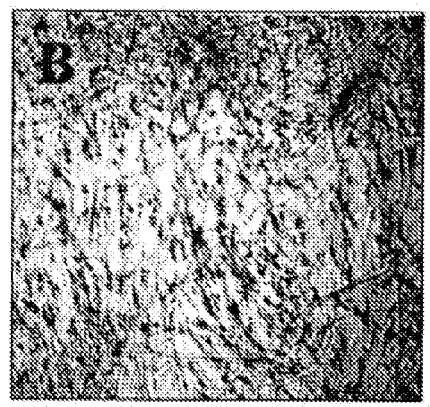
Figure 4C:
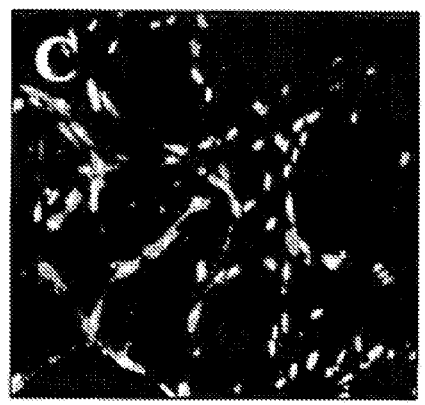
Figure 4D:
Figure 4G:
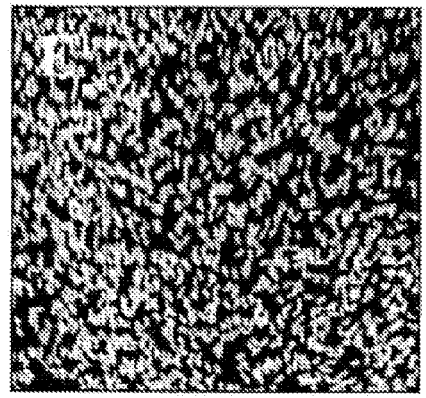
Figure 4G:
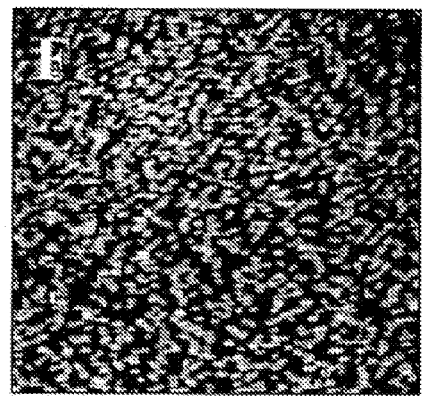
Figure 4G:
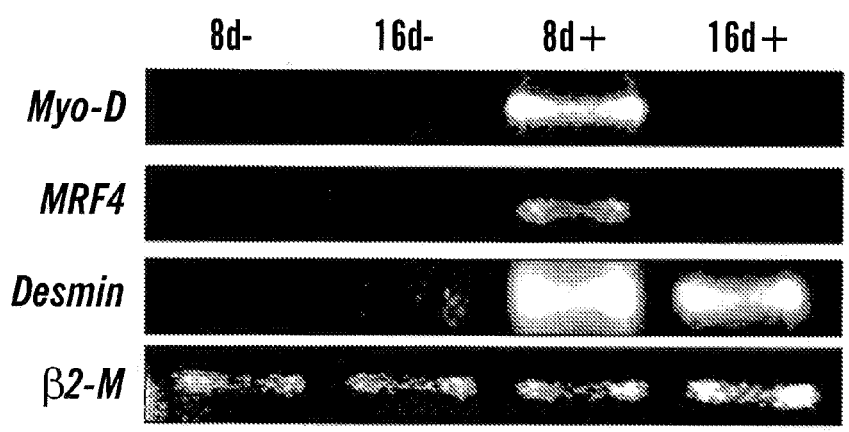
Figure 5A:
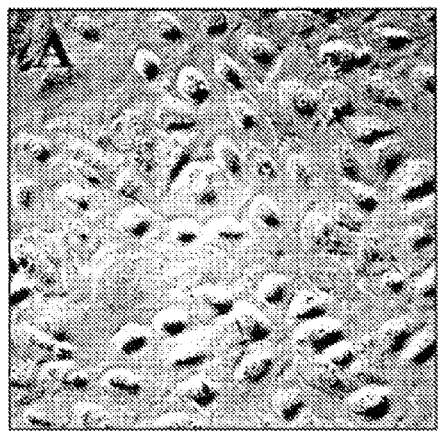
Figure 5B:
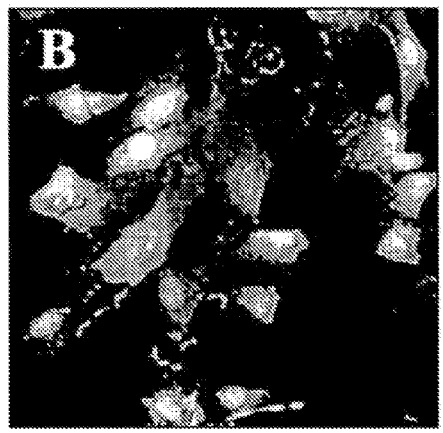
Figure 5C:
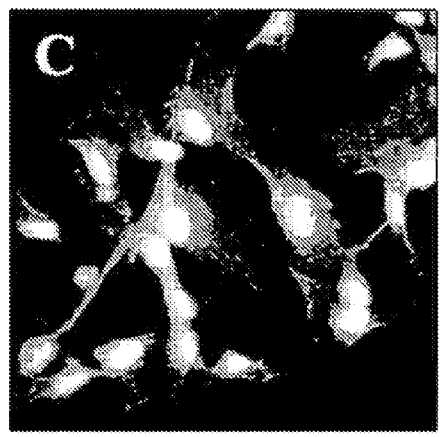
Figure 5D:
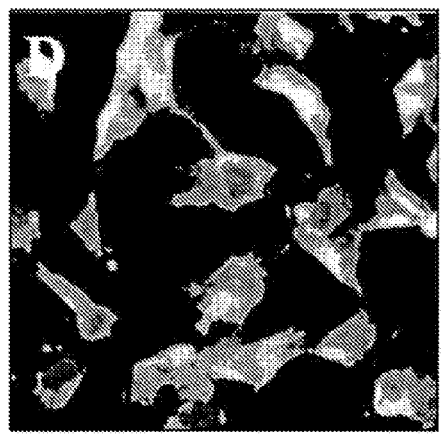
Figure 5E:
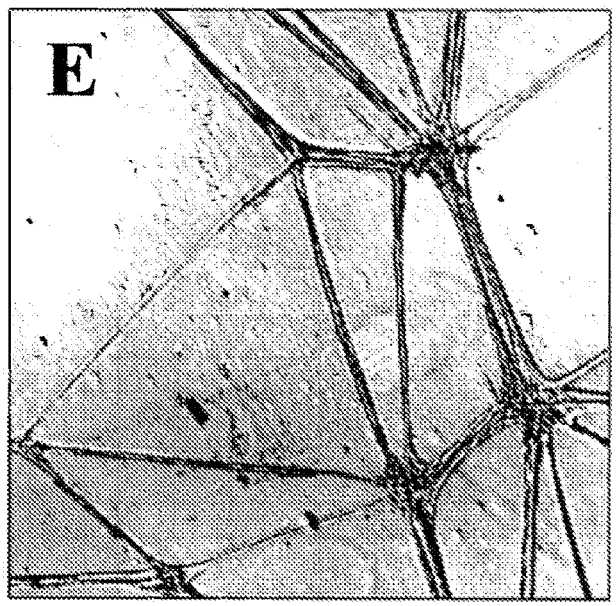
Figure 5F:
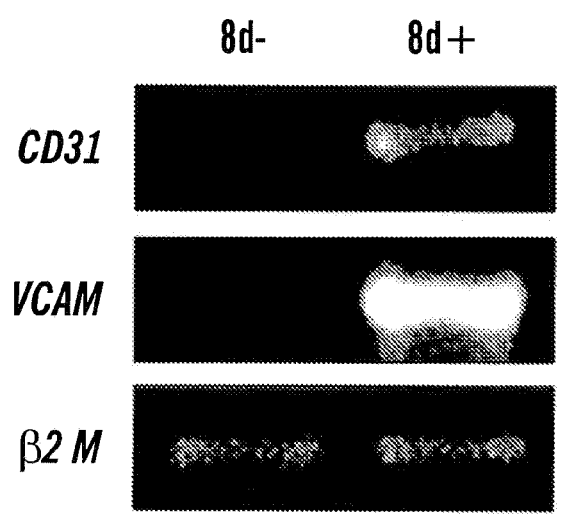
Figure 6A:
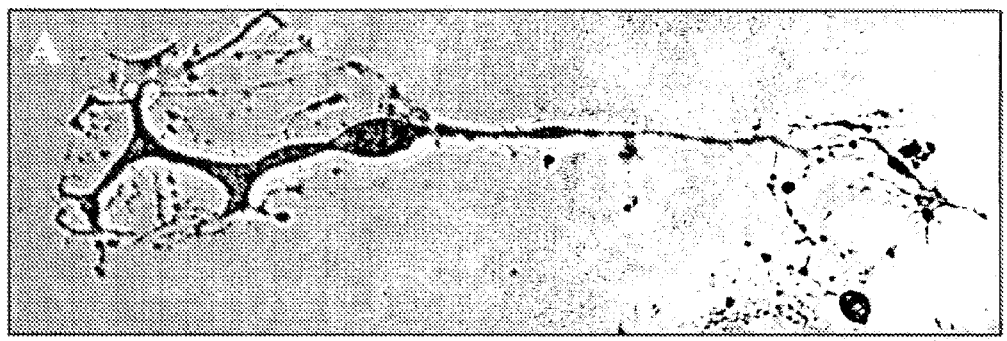
Figure 6B:
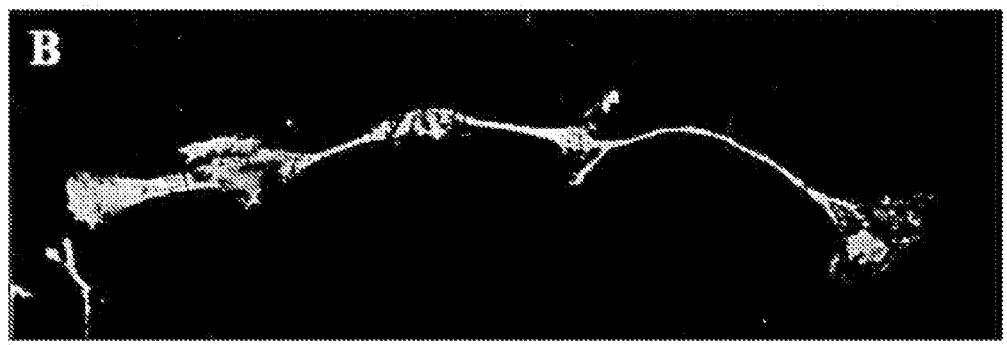
Figure 6E:
Figure 6E:
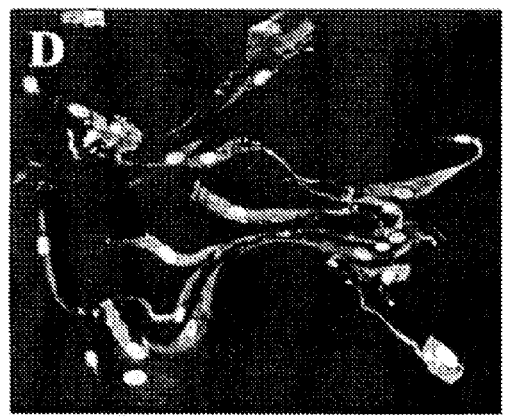
Figure 6E:
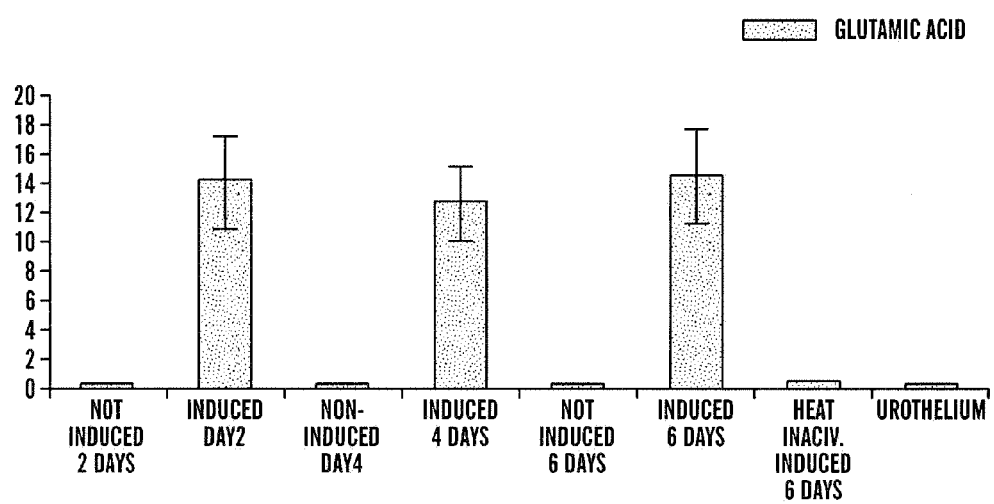

Induction with 5-azacytidine for 24 hours induced the formation of multinucleated cells after a 24 to 48 hour period [FIG. 4A]. The multinucleated cells expressed the muscle differentiation markers desmin and sarcomeric tropomyosin. [FIGS. 4D and F]. C-kit$^{pos}$ cells grown in control medium and c-kit$^{pos}$ cells grown in myogenic conditions did not lead to cell fusion or multinucleated cells.

We analyzed the expression of MyoD, Myf 6 (MRF4) and Desmin in cells undergoing myogenic differentiation, using RT-PCR. A characteristic pattern of gene expression, reflecting that seen with embryonic muscle development, was demonstrated [FIG. 4G] (32, 33). Previous studies in mouse embryos have shown that Myf6 is expressed transiently between days 9 and 11 (34, 35). In our study Myf6 was expressed at day 8 and suppressed at day 16. As has been shown with ES cells, MyoD expression was detectable at 8 days and suppressed at 16 days in the c-kit$^{pos}$ cells grown under myogenic conditions. Desmin expression was induced at 8 days and increased by 16 days in the c-kit$^{pos}$ cells cultured in myogenic medium. In contrast, there was no activation of Myf6, MyoD or Desmin in the control cells at 8 and 16 days.

C-kit$^{pos}$ cells were labeled with a fluorescence marker (PKH26 Green Fluorescent Cell Linker, Sigma-Aldrich) and were induced into a myogenic lineage. The myogenic cells were resuspended in rat tail collagen containing 17% Matrigel (BD Biosciences), were injected into the hindlimb musculature of athymic mice, and were retrieved after 4 weeks. The injected myogenic cells showed the formation of muscle tissue which express desmin (A) and maintained its fluorescence (B) [FIG. 4].

Endothelial induction. To induce endothelial differentiation, we plated the cells in dishes precoated with PBS-gelatin. The cells were maintained in culture for 1 month in endothelial-defined medium. To induce endothelial differentiation, the cells were plated at a density of 3000 cells/cm$^2$ in 35 mm dishes precoated with PBS-gelatin. The cells were maintained in culture for 1 month in endothelial basal medium-2 (EBM-2 Clonetics BioWittaker inc., Walkersville, Md.) supplemented with 10% FBS (GIBCO/BRL, Grand Island, N.Y.), 1% antibiotics (GIBCO/BRL, Grand Island, N.Y.) and 1% L-glutamine (GIBCO/BRL, Grand Island, N.Y.). Basic fibroblast growth factor (bFGF) was added every other day. After 1 week in culture the c-kit$^{pos}$ cells changed their morphology, and by the second week, the cells were mostly tubular [FIG. 5A]. Human-specific endothelial cell For hepatic differentiation, c-kit$^{pos}$ cells surface markers (P1H12), factor VIII (FVIII) and KDR are specific for differentiated endothelial cells. The differentiated cells stained positively for FVIII, KDR and P1H12 [FIG. 5B-D]. C-kit$^{pos}$ cells cultured in Chang medium for the same period of time were not able to form tubular structures and did not stain for endothelial specific markers. Endothelial cells are usually difficult to isolate and maintain in culture. In our study the endothelial cells, once differentiated, were able to grow in culture and formed capillary-like structures in vitro [FIG. 5E]. In order to confirm the phenotypic changes we performed RT-PCR. Platelet endothelial cell adhesion molecule 1 (PECAM-1 or CD31) and vascular cell adhesion molecule (VCAM) were markedly increased in the ckit$^{pos}$ cells induced in endothelial media but were not amplified in the ckit$^{pos}$ cells cultured in control media [FIG. 5F].

Hepatic induction. For hepatic differentiation, c-kit$^{pos}$ cells from amniotic fluid and chorionic villi, seeded in Matrigel coated dishes, were cultured in hepatic condition for 9 days. The c-kit$^{pos}$ cells seeded in Matrigel (Collaborative Biomedical Products, Universal Biologicals Ltd.) using a modified manufacturer thin gel method using 100 ul/cm$^2$ surface. The cells seeded in 24-well plates at a density of 25,000 cells/cm$^2$ were allowed to establish themselves in this culture in Chang medium for 3 days to achieve a semi-confluent density. Differentiation was induced in three steps. The base medium consisted of low glucose Dulbecco's medium (Gibco/Brl) containing 300 uM monothioglycerol (Sigma-Aldrich), 100 U/ml penicillin, and 100 U/ml streptomycin (Gibco/Brl) with 15% fetal bovine serum FBS, (Gibco/Brl). Cells were grown initially for 3 days in the presence of 100 ng/ml acidic fibroblastic growth factor ( ). This step was followed by exposure to 20 ng/ml hepatocyte growth factor ( ) for 3 days and concluded with 20 ng/ml hepatocyte growth factor, 10 ng/ml oncostatin M ( ), 10-7 M dexamethasone (Sigma-Aldrich)[1]. Cells were maintained in the same media used for end stage differentiation. Control cell populations were seeded in the same manner as differentiated cells, but were simply maintained in control medium. After the differentiation process the cells were maintained in culture for 30 days.

In order to evaluate the hepatic differentiation, the expression of albumin was evaluated and the urea production was measured using a standard urea nitrogen essay in the differentiated cells and in the control cells. Cells suspended in matrigel were trypsanized for 10 minutes with light mechanical assistance and cytospin onto slides at a density of 1000 cells/slide. Cells were probed for albumin with goat anti-human albumin ( ) using standard immunocytochemistry protocol with DAPI nuclear counterstain. Urea production was measured using a colorometric urea nitrogen assay (Sigma-Aldrich). Differentiated or control cell populations were placed in ammonium chloride at a supraphysiological level of 20 mM NH4Cl to examine maximum rate of urea production of each of these cell types. The medium was then collected after 30 minutes of exposure and tested per manufacturer instructions with and without urease to obtain true levels of urea. After 7 days of the differentiation process, cells tended to show morphological changes from elongated fibroblastic cells to more epitheliod cobblestone appearances. Cells showed positive staining for at day 12 post differentiation. The maximum rate of urea production for hepatic differentiation induced cells was $4.7 \times 10^{-4}$ µg urea/hour/cell as opposed to $2.36 \times 10^{-4}$ µg urea/hour/cell for control cell populations.

Neurogenic induction. For neurogenic induction, we cultured amniotic and chorionic villi ckit$^{pos}$ cells in defined neurogenic medium (40, 41). For neurogenic induction, the amniotic cells were seeded at a concentration of 3000 cells/cm$^2$ in 100 mm plates and were cultured in DMEM low glucose medium (GIBCO/BRL, Grand Island, N.Y.), 1% antibiotics (GIBCO/BRL, Grand Island, N.Y.), 2% DMSO and 200 µM butylated hydroxyanisole (BHA, Sigma-Aldrich, St. Louis, Mo.). Neuron growth factor (NGF) (8 µl/ml) was added to the culture every 2 days. After 2 days the medium was changed to control medium and the same amount of NGF was continuously supplemented. Cells were fixed for immunocytochemestry at 4 and 8 days.

After 2 days the medium was changed to control medium and the same amount of NGF was continuously supplemented. Cells were fixed for immunocytochemistry at 4 and 8 days. Control medium consisted of modified αMEM. Medium changes were performed every 3 days.

C-kit$^{pos}$ cells cultured in neurogenic conditions changed their morphology within the first 24 hours. Two different cell populations were apparent, morphologically large flat cells and small bipolar cells. The bipolar cell cytoplasm retracted towards the nucleus, forming contracted multipolar structures. Over the subsequent hours, the cells displayed primary and secondary branches and cone-like terminal expansions [FIG. 6A]. Induced C-kit$^{pos}$ cells showed a characteristic sequence of expression of neural-specific proteins. At an early stage the intermediate filament protein nestin (BD Bioscience), which is specifically expressed in neuroepithelial stem cells, was highly expressed [FIG. 6B]. The expressions of β III tubulin [FIG. 6C] and glial fibrillary acidic protein (GFAP) (Santa Cruz) [FIG. 6D], markers of neuron and glial differentiation (42), respectively, increased over time and seemed to reach a plateau at about 6 days. C-kit$^{pos}$ cells cultured in Chang medium and c-kit$^{neg}$ cells cultured in neurogenic medium for the same period did not stain for neurogenic specific markers. Furthermore we analyzed the functional behavior of the neuronal cells. The C-kit$^{pos}$ cells cultured under neurogenic conditions showed the presence of the neurotransmitter glutamic acid in the collected medium. Glutamic acid is usually secreted by fully differentiated neurons in culture (43). Non-induced cells, heat inactivated cells and control urothelial cells did not secrete any glutamic acid [FIG. 6E].

Hematopoietic differentiation. For the hematopoietic differentiation we used a liquid media (StemSpan by STEM CELL TECHNOLOGIES, see www.stemcell.com). The following frowth factors were added to the cell culture medium: stem cell factor, GM-CSF, IL6, IL3, G-CSF according to the manufacturer's instructions (STEM CELL TECHNOLOGIES). The hematopoietic differentiation was assessed by analyzing the cell morphology.

Murine chorionic villi and amniotic fluids were collected from female C57BL/6 mice that were from 6 to 9 weeks of age and that were 12 days pregnant (protocol approved Animal Care and Use Committee, Children's Hospital, Boston) under light microscopy. The samples were proceeded as previously described. Briefly placentas were dissected under light microscope and the chorionic villi were explanted. Chorionic villi and amniotic fluid derived cells were cultured in the same conditions used for human cells with addition of LIF (10 ng/ml) (Sigma-Aldrich). The ckit$^{pos}$ cells were transduced with a puc-CMMP-IC-eGFP retrovirus and expanded. The infected-cKit$^{pos}$ were sorted by FACS-Excalibur and a single eGFP$^+$-cells was plated per well in a 96 wells-plate and expanded.

In order to assess the ability of these cells to contribute to different tissue 10-12 ckit$^{pos}$ infected cells were microinjected into 4-day-old blastocysts of C57BL/6-TgN(lacZpl) 60Vij. The blastocysts were transferred to foster mothers and mice were allowed to develop until 16 days of gestation.

The fetuses were collected, embedded in OCT and 10 µm whole-body sections were prepared. Tissue sections were stained for β-galactosidase enzyme activity and observed under fluorescent microscope in order to identify the c-kit$^{pos}$ cells carrying the gene for the green protein.

We also collected multiple organs, they were embedded in OCT and 5 µm sections were prepared as described. The sections were stained for β-galactosidase enzyme activity and observed.

Frozen section were cut at 10 µm and fixed with 2% formaldehyde, 0.2% glutaraldehyde, 0.02% NP-40 and 0.01% sodium deoxycolate in PBS pH7.8 for 30 min at RT and then wash 3 times with PBS. Samples were incubated in LacZ staining solution (2 mM MgCl2, 0.02% NP-40, 0.01% sodium deoxycolate, 5 mM K-ferricyanide, 5 mM K-ferrocyanide and 0.1% X-gal in PBS pH7.8) at 37 C for 8 to 16 hours in dark. Images were acquired using IX-70 microscope with Magna Fire Digital Imaging Camera System (Olympus) and processed using Adobe Photoshop 5.0.

Discussion. Stem cells have been reported to exist during embryonic development and postnatally, in bone marrow, skeletal muscle and skin (for a recent review discussion of stem cells see, J. Pathol, Vol 197, Issue 4, 2002). Embryonic stem (ES) cells are derived from the inner cell mass (ICM) at the blastula stage. ES cells tend to differentiate spontaneously into various types of tissues. However, isolation of these cells, particularly from human embryos, has resulted in heated debate about ethical concerns of this procedure which results in destruction of the embryo.

Adult stem cells do not differentiate spontaneously, but can be induced to differentiate by applying appropriate growth conditions. Adult stem cells seem to be easier to maintain in culture than ES cells. However, adult stem cells have the disadvantage of not being immortal, and most of them lose their pluripotency after a defined number of passages in culture. This short life-span is a significant obstacle in clinical applications where a large amount of cells are needed.

Fetal tissue has been used in the past for transplantation and tissue engineering research because of its pluripotency and proliferative ability. Fetal cells have a higher proliferative capacity than adult cells and may preserve their pluripotency longer in culture. However, there are several issues concerning the availability of fetal cell transplants. Beyond the ethical concerns regarding the use of cells from aborted fetuses or living fetuses, there are other issues, which remain a challenge. For example, previous studies have shown that up to six fetuses are required to provide enough material to treat one patient with Parkinson's disease (45).

This invention is based upon a finding that chorionic villi and amniotic fluid cells, which have been used for decades for prenatal diagnosis, represent a viable source of human fetal stem cells from both embryonic and fetal sources and can be used therapeutically. It is well known that both chorionic villi tissue specimens and amniotic fluid contain a large variety of cells. The vast majority of the cells collected from chorionic villi and amniotic fluid are already differentiated, and therefore have a limited proliferative ability (46). We have here identified and isolated cells that maintained both their pluripotential and proliferative ability.

Many efforts in the past were aimed at trying to identify antibodies that bind cell surface markers on undifferentiated cells. C-kit, CD105, CD34 and CD90 have been identified as potential stem cell markers. We found that less than 1% of the embryonic and fetal cells isolated from chorionic villi and amniotic fluid were c-kit$^{pos}$ and that only the isolated c-kit$^{pos}$ cells had the pluripotent phenotype. The c-kit gene encodes for a tyrosine kinase growth factor receptor for Stem Cell Factor (SCF), also called mast cell growth factor that is essential for hematopoesis, melanogenesis and fertility (46). The Kit protein (CD117) is constitutively expressed in hematopoietic stem cells, mast cells, germ cells, melanocytes, certain basal epithelial cells, luminal epithelium of breast, and the interstitial cells of Cajal of the gastrointestinal tract (47). The c-kit gene plays a fundamental role during the establishment, maintenance and function of germ cells (48). In the embryonal gonad, the c-kit receptor and its ligand SCF are required for the survival and proliferation of primordial germ cells. Furthermore recent studies have shown that c-kit is expressed in placental tissue during pregnancy. C-kit and SCF may have an important role in embryonic development as evidenced by expression and localization at the feto-maternal interface (49). In the postnatal animal, c-kit/SCF are required for production of the mature gametes in response to gonadotropic hormones, i.e. for the survival and/or proliferation of the only proliferating germ cells of the testis, the spermatogonia, and for the growth and maturation of the oocytes. Experiments in vitro have shown that c-kit is a potent mitogen for primitive hematopoetic cells. In mice, loss of either SCF or c-kit results in macrocytic anemia, leading to death in-utero or within the first postnatal days.

Adult stem cells have a limited capacity to proliferate and they undergo senescence when the Hayflick limit is reached. Furthermore, the adult stem cells are not able to preserve their ability to differentiate into multiple lineages after a few passages. Contrary to adult stem cells, embryonic stem (ES) cells have an unlimited capacity to proliferate and they are able to maintain their potential for differentiation in culture. We found that the c-kit$^{pos}$ cells derived from human embryonic and fetal chorionic villi and amniotic fluid were pluripotent and were able to differentiate into osteogenic, adipogenic, myogenic, neurogenic, hepatic and endothelial phenotypes. The possibility of forming different types of tissues was confirmed in vivo. The cells were telomerase positive, highly clonogenic, and the cloned fetal stem cell lines were able to undergo more than 250 cell divisions, exceeding Hayflick's limit. The stem cell lines maintained their telomere length and differentiation potential in culture, even after 250 population doublings. In addition, the c-kit$^{pos}$ cells did not require a feeder layer for growth. The c-kit positive human fetal stem cells also expressed markers known to be associated with human embryonic stem cells (SSAE3 and SSAE4).

In conclusion, we describe the isolation, expansion and differentiation of stem cells from human embryonic and fetal chorionic villi and amniotic fluid. These cells provide an excellent source for both research and therapeutic applications. Embryonic and fetal stem cells have a better potential for expansion than adult stem cells and for this reason they represent a significantly better source for therapeutic applications where large numbers of cells are needed.

Further, the ability to isolate stem cells during gestation may also be advantageous for treatment of fetuses with congenital malformations in utero. When compared with ES cells, c-kit$^{pos}$ fetal stem cells isolated from chorionic villi and amniotic fluid have many similarities: they can differentiate into all three germ layers, they express common markers and show telomerase activity. However c-kit$^{pos}$ cells isolated from the chorionic villi and amniotic fluid have considerable advantages over ES cells. The c-kit$^{pos}$ cells isolated from the chorionic villi and amniotic fluid easily differentiate into specific cell lineages, they do not need feeder layers to grow, and most importantly, the isolation of these cells does not require the sacrifice of human embryos for their isolation, thus avoiding the current controversies associated with the use of human embryonic stem cells.

The references cited herein and throughout the specification are incorporated by reference in their entirety.

REFERENCES

1. Pittenger, M. F., et al., Science 284(5411), p. 143 (1999).
2. Thomson, J. A., et al., Proc. Natl. Acad. Sci. USA, 92(17), p. 7844 (1995).
3. Reubinoff, B. E., et al., Nature Biotechnol., 18(4), p. 399 (2000).
4. Munn, D., Science, 293(5528), p. 211 (2001).
5. P. De Coppi, G. Schuch, A. Atala, *Fetal cell culture in Methods of Tissue Engineering*, A. Atala, R. P. Lanza, R. P. 2002 (San Diego: Academic Press. Cap.) cap. 71 p. 875.
6. Cremer, M., et al., Hum. Genet., 59(4), p. 373 (1981).
7. J. H. Priest, *Prenatal Chromosomal Diagnosis and Cell Culture* in *The ACT Cytogenetics Laboratory Manual*, Margaret J. Barch (Raven Press, New York ed. 2, 1991) cap.5 p. 149.
9. von Koskull, H., et al., Prenat. Diagn., 1(4), p. 259 (1981).
10. Medina-Gomez, P. and T. H. Johnston, Hum. Genet., 60(4), p. 310 (1982).
12. Thomson, J. A., et al., Science, 282(5391), p. 1145 (1998).
15. Kim, N. W., et al., Science, 266(5193), p. 2011 (1994).
16. Reddel, R. R. et al., (1997). Immortalized cells with no detectable telomerase activity. Biochemistry 62, 1254-1262.
17. Bryan, T. M. et al (1995). Telomere elongation in immortal human cells without detectable telomerse activity. EMBO J. 14, 4240-4248.
18. Bryan, T. M et al (1998) Exp Cell Res. March 15; 239(2): 370-8.
24. Karsenty, G., Semin. Cell Dev. Biol., 11(5), p. 343 (2000).
25. Komori, T., et al., Cell, 89(5), p. 755 (1997).
28. Kim, J. B., et al., Proc. Natl. Acad. Sci. USA, 95(8), p. 4333 (1998).
29. Rosen, E. D., et al., Mol. Cell, 4(4), p. 611 (1999).
30. Ferrari, G., et al., Science, 279(5356), p. 1528 (1998).
32. Rohwedel, J., et al., Dev. Biol., 164(1), p. 87 (1994).
33. Bailey, P., T. Holowacz, and A. B. Lassar, Curr. Opin. Cell Biol., 13(6), p. 679 (2001).
34. Hinterberger, T. J., et al., Dev. Biol., 147(1), p. 144 (1991).
35. Patapoutian, A., et al., Development, 121(10), p. 3347 (1995).
40. Woodbury, D., et al., J. Neurosci. Res., 61(4), p. 364 (2000).
41. Black, I. B. and D. Woodbury, Blood Cells Mol. Dis., 27(3), p. 632-6. (2001).
42. Guan, K., et al, Cell Tissue Res., 305(2), p. 171 (2001).
43. Carpenter M. K., et al, Exp. Neurol. 158, 266 (1999).
44. Fine, A., Cmaj, 151(9), p. 1261 (1994).
45. Sarkar, S., et al., Am. J. Obstet. Gynecol., 136(1), p. 67 (1980).
46. Ashman, L. K., Int. J. Biochem. Cell Biol., 31(10), p. 1037 (1999).
47. Shimizu, M., et al., Exp. Cell Res., 266(2), p. 311-22 (2001).
48. Robinson, L. L., et al., Mol. Hum. Reprod., 7(9), p. 845 (2001).
49. Mitsunari, M., et al., Mol. Hum. Reprod., 5(9): p. 874 (1999).

What is claimed is:

1. A method of proliferating a population of cells enriched for human pluripotent fetal stem cells comprising:
    (a) selecting at least one c-kit positive cell from a human amniotic fluid sample, wherein said cell is c-kit, SSEA3 and SSEA4 positive, and immunonegative for SSEA1;
    (b) introducing said at least one selected cell to a culture medium; and
    (c) proliferating said at least one selected cell in the culture medium.

2. A method of obtaining a composition enriched for human pluripotent fetal stem cells, said cells being c-kit, SSEA3 and SSEA4 positive, and SSEA1 negative, comprising the steps of:
    (a) cryopreseverving a specimen of the amniotic fluid;
    (b) thawing the cryopreserved specimen at a later date; and
    (c) selecting for c-kit positive cells.

3. A method of producing a composition enriched for human pluripotent fetal stem cells, said cells being c-kit, SSEA3 and SSEA4 positive, and SSEA1 negative comprising,
    (a) isolating c-kit positive cells from a sample of amniotic fluid; and
    (b) proliferating said cells in culture medium.

4. A method of obtaining a composition enriched for human pluripotent fetal stem cells that are c-kit, SSEA3 and SSEA4 positive, and SSEA1 negative comprising selecting c-kit positive cells from a human amniotic fluid sample.

5. The method of claim 4, wherein the selecting c-kit positive cells is performed using an antibody against c-kit.

6. The method of claim 5, wherein the antibody against c-kit is a monoclonal antibody.

7. The method of claim 5, wherein the monoclonal antibody against c-kit is a mouse monoclonal IgG against an antigenic epitope of human c-kit.

8. The method of claim 5, wherein the antibody against c-kit is fluorochrome conjugated.

9. The method of claim 5, wherein the antibody against c-kit is conjugated to magnetic particles.

10. The method of claim 4, wherein the selecting is by flow cytometry.

11. The method of claim 4, wherein the selecting is by fluorescence activated cell sorting or high gradient magnetic selection.

12. The method of claim 4, wherein the amniotic fluid sample is cryopreserved prior to the selection step.

13. The method of claim 4, further comprising cyropreserving the c-kit, SSEA3 and SSEA4 positive, and SSEA1 negative cells.

14. A method of producing a composition enriched for human pluripotent fetal cells comprising:
    (a) selecting at least one c-kit positive cell from a human amniotic fluid sample, wherein said cell is c-kit, SSEA4, and telomerase positive;
    (b) introducing said at least one selected cell to a culture medium; and
    (c) proliferating said at least one selected cell in the culture medium.

* * * * *